US007176239B2

(12) United States Patent
Wang et al.

(10) Patent No.: US 7,176,239 B2
(45) Date of Patent: Feb. 13, 2007

(54) **METHODS AND COMPOSITIONS FOR TREATMENT OF *ATAXIA-TELANGEICTASIA***

(75) Inventors: Suming Wang, 15138 Rosewood Dr., Clive, IA (US) 50325; Rodney E. Shackelford, Shreveport, LA (US)

(73) Assignee: Suming Wang, Clive, IA (US)

( * ) Notice: Subject to any disclaimer, the term of this patent is extended or adjusted under 35 U.S.C. 154(b) by 695 days.

(21) Appl. No.: 10/617,943

(22) Filed: Jul. 11, 2003

(65) Prior Publication Data
US 2005/0009760 A1    Jan. 13, 2005

(51) Int. Cl.
*A61K 35/42* (2006.01)
*A61K 35/55* (2006.01)

(52) U.S. Cl. ...................... 514/557; 514/566

(58) Field of Classification Search ............... 514/557, 514/566
See application file for complete search history.

(56) References Cited

OTHER PUBLICATIONS

Shackelford et al. Desferrioxamine treatment increases the genomic stability of *Ataxia-telangiectasia* cells, DNA Repair, Sep. 18, 2003, vol. 2, pp. 971-981.*
Weil et al., Radiation Induces Genomic Instability and Mammary Ductal Dysplasia in ATM Heterozgous Mice, 2001, Oncogene, vol. 20, 4409-4411.*
Shackelford, Rodney et al. "Desferrioxamine treatment increases the genomic stability of *Ataxia-telangiectasia* cells" ScienceDirect, DNA Repair, vol. 2, Issu 9, Sep. 2003, pp. 971-981.
Simpson, Marty "Buck Researcher Links Iron to Parkinson's Disease" Buck Institute, Neuron Mar. 26, 2003.
Polla, Ada S., et al. "Iron as the malignant spirit in successful ageing" Ageing Research Reviews 2(2003) 25-37.

Young, Ian.S., et al. "The effects of desferrioxamine and ascorbate on oxidative stress in the streptozotocin diabetic rat" ScienceDirect, Free Radical Biology and Medicine, vol. 18, Issue 5, May 1995, pp. 833-840.
Kaur, Deepinder et al. "Genetic or Pharmacological Iron Chelation Prevents MPTP-Induced Neurotoxicity In Vivo" Science Direct, Neuron, vol. 37, Issue 6, Mar. 27, 2003, pp. 899-909.
Wong, Alice PhD, et al. "Oxidative Stress in Friedreich's *Ataxia*: Mechanisms and Potential Therapy" Friedreich's *Ataxia* (FRDA) NAF 1999.
Naughton, D.P., "Iron(III)-mediated intra-articular crystal deposition in arthritis: a therapeutic role for iron chelators" ScienceDirect, Medical Hypotheses, vol. 57, Issue 1, Jul. 2001, pp. 120-122.
Duffy, SJ, et al. "Iron chelation improves endothelial function in patients with coronary artery disease." Entrez-Pub-Med, Abstract Jun. 12, 2001.
Kuperstein, Faina et al., "Pro-apoptotic signaling in neuronal cells following iron and amyloid beta peptide neurotoxicity" Journal of Neurochemistry, vol. 86, No. 1, 2003 114-125.
Cameron, NE., et al. "Neurovascular dysfunction in diabetic rates. Potential contribution of autoxidation and free radicals examined using transition metal chelating agents." ABSTRACT Entrez-PubMed, J. Clin. Invest. Aug. 1995;96(2); 1159-63.
Buss, Joan L., et al. "The Role of Iron Chelation in Cancer Therapy" Abstract—Currently Medicinal Chemistry, vol. 10, No. 12, 2003.

* cited by examiner

*Primary Examiner*—Johann Richter
*Assistant Examiner*—Nikki Handy
(74) *Attorney, Agent, or Firm*—McKee, Voorhees & Sease, P.L.C.

(57) ABSTRACT

This invention relates to the methods and pharmaceutical compositions for treating diseases or disorders associated with oxidative stress and/or genomic instability. In particular, the invention relates to methods for treating ataxia-telangeictasia (AT) and such disease states by administering a therapeutically effective amount of a chelating agent to increase genomic stability and/or decrease oxidative stress.

43 Claims, 25 Drawing Sheets

METHODS AND COMPOSITIONS FOR TREATMENT OF *ATAXIA-TELANGEICTASIA*

FIELD OF INVENTION

This invention relates to the methods and pharmaceutical compositions for treating diseases or disorders associated with oxidative stress and/or genomic instability. In particular, the invention relates to methods for treating ataxia-telangeictasia (AT) and such disease states by administering a therapeutically effective amount of a chelating agent and/or antioxidant to increase genomic stability and/or decrease oxidative stress.

BACKGROUND OF THE INVENTION

Ataxia-telangeictasia (AT) is a degenerative brain disease in children, characterized by immune dysfunction, oculocutaneous telangiectasias, cerebellar degeneration accompanied by ataxia, a high incidence of lymphoreticular cancers, and other cell cycle abnormalities. (M. F. Lavin, Y. Shiloh, The Genetic Defect in Ataxia-telangiectasia, 15 ANNU. REV. IMMUNOL. 177–202 (1997).) A-T is an autosomal recessive disorder, with an average worldwide frequency of 1:40,000–1:100,000 live births. AT manifests itself during childhood and most individuals affected with AT die in their adolescence or early adulthood due to infections or cancer.

One of the hallmarks of AT is a predisposition to cancer. 38% of AT patients develop malignancies, mainly lymphoreticular neoplasms and leukemias. AT heterozygotes are reported to have an increased risk of developing breast cancer. (M. M. Weil et al. Radiation Induces Genomic Instability and Mammary Ductal Dysplasia in ATM Heterozygous Mice, 20(32) ONCOGENE 4409–11 (2001).) Although highly predisposed to develop cancer, AT patients are limited with respect to treatment options due to genomic instability. Genomic instability—also called "genetic instability" and "chromosomal instability"—refers to the failure of a cell to maintain its genome. Genomic instability can be initiated and intensified by complex DNA damage, oxidative stress, DNA repair deficiencies, loss of cell cycle checkpoint, and disruption to telomeres. In AT, these conditions have been shown to exacerbate genomic instability.

As mentioned previously, AT patients suffer from genomic instability and, therefore, are not good candidates for traditional methods used to treat cancerous cells. AT patients are hypersensitive to DNA damaging agents, such as radiomimetic chemotherapy, and therapeutic, ionizing radiation (IR) that increase the level of reactive oxidation species (ROS). For example, in vitro studies show that fibroblasts and lymphoblasts from AT homozygotes show sensitivity to a number of radiomimetic and free-radical-producing agents. (Y. Shiloh et al. In Vitro Phenotype of Ataxia-telangiectasia (AT) Fibroblast Strains: Clues to the Nature of the "AT DNA Lesion" and the Molecular Defect in AT, 19 KROC FOUND SER. 111–21 (1985); Y. Shiloh et al. Cells from Patients with Ataxia telangiectasia Are Abnormally Sensitive to the Cytotoxic Effect of a Tumor Promoter, Phorbol-12-Myristate-13-Acetate, 149(2) MUTAT RES. 283–86 (1985).) An increase in the ROS levels above a certain threshold, often referred to as oxidative stress, is accompanied by processes that are harmful for cell survival, such as lipid peroxidation and oxidative modification of proteins and nucleic acids.

Oxidative stress has been implicated as a major contributor to AT as well as many other diseases and degenerative conditions including aging, cancer, arthritis, cardiovascular disease, Alzheimer's disease, and diabetes. In fact, individuals with AT exhibit increased markers of oxidative stress, including lipid peroxidiation and oxidative damage to DNA. Evidence indicates that AT is in part, a disease involving chronic oxidative stress, diminished antioxidant capacity, and inability to respond appropriately to exogenous oxidants. (A. Barzilai et al. ATM Deficiency and Oxidative Stress: a New Dimension of Defective Response to DNA Damage, 1 DNA REPAIR 3–25 (2002).) For example, AT cells show increased lipid peroxidation, lowered catalase activity, lowered manganese superoxide dismutase levels, and delay of glutathione resynthesis after depletion with diethylpyrocarbonate. (D. Watters et al. Localization of a Portion of Extranuclear ATM to Peroxisomes, 274 J. BIOL. CHEM. 34277–34282 (1999); M. J. Meredith & M. L. Dodson, Impaired Glutathione Biosynthesis in Cultured Human Ataxia-telangiectasia Cells, 47 CANCER RES. 4576–4581 (1987).) AT cells also show increases in genotoxic stress-induced proteins which are lowered by treatment with the antioxidant a-lipoic acid, indicating that AT cells are under chronic oxidative stress. (M. Gatei et al. Ataxia-telangiectasia: Chronic Activation of Damage-Responsive Functions Is Reduced By Alpha-lipoic Acid, 20 ONCOGENE 289–294 (2001).) Similarly, individuals with AT exhibit increased markers of oxidative stress, including lipid peroxidaton and 8-hydroxydeoxyguanosine. (J. Reichenback et al. Elevated Oxidative Stress in Patients with Ataxia Telangiectasia, 4 ANTIOXIDANTS REDOX. SIG. 465–469 (2002).) AT knockout mice show a similar pathophysiology, particularly in the cerebellum. (A. Kamsler et al. Increased Oxidative Stress in Ataxia-telangiectasia Evidenced by Alterations in Redox State of Brains from Atm-deficient Mice, 61 CANCER RES. 1849–1854 (2001); Y. Ziv et al. 15 Recombinant ATM Protein Complements the Cellular A-T Phenotype, ONCOGENE 159–167 (1997).) In vitro, AT cells are unusually sensitive to the toxic effects of exogenous oxidants, including hydrogen peroxide, tert-butyl hydroperoxide (t-BOOH), nitric oxide, hexavalent chromium, arsenic, and superoxide. (R. E. Shackelford et al. The Ataxia telangiectasia Gene Product Is Required for Oxidative Stress-induced G1 and G2 Checkpoint Function in Human Fibroblasts, 276 J. BIOL. CHEM. 21951–21959 (2001); L. Ha et al. Chromium (VI) Activates Ataxia Telangiectasia Mutated (ATM) Protein. Requirement of ATM for Both Apoptosis and Recovery from Terminal Growth Arrest, 278 J. BIOL. CHEM. 17885–17894 (2003); L. J. Hofseth et al. Nitric Oxide-induced Cellular Stress and p53 Activation in Chronic Inflammation, 100 PROC. NATL. ACAD. SCI. USA 143–148 (2003); M. H. L. Green et al. Hypersensitivity of Ataxia-telangiectasia Fibroblasts to a Nitric Oxide Donor, 22 FREE RADICAL BIOL. MED. 343–347 (1997); M. Vuillaume et al. Stimulated Production of ATP by H2O2 Disproportionation in Extracts from Normal and Xeroderma Pigmentosum Skins, and from Normal, Xeroderma Pigmentosum, Ataxia telangiectasia and Simian Virus 40 Transformed Cell Lines, 10 CARCINOGENESIS 1375–1381 (1989); A. J. Ward et al. Response of Fibroblast Cultures from Ataxia-telangiectasia Patients to Reactive Oxygen Species Generated During Inflammatory Reactions, 24 ENVIRON. MOL. MUTAGEN. 103–111 (1994); D. Menendez et al. ATM Status Confers Sensitivity to Arsenic Cytotoxic Effects, 16 MUTAGENESIS 443–448 (2001).)

Individuals with AT also present other characteristics associated with genomic instability, that of DNA repair deficiencies, disruption to telomeres and loss of cell cycle checkpoint. In vitro studies using cells from individuals with AT show defects in these areas when compared to normal cells. For example, cells from AT patients have a decreased frequency of repairing broken chromosomes compared to normal cells. (M. Martin et al. Radiation-induced Chromosome Breaks in Ataxia-telangiectasia Cells Remain Open, 79(3) INT. J. RADIAT BIOL. 203–10 (2003).) AT cells subjected to mild chronic oxidative stress show an increase in the rate of telomere shortening compared to normal fibroblasts. (A. Tchirkov & P. M. Lansdorp. Role of Oxidative Stress in Telomere Shortening in Cultured Fibroblasts from Normal Individuals and Patients with Ataxia-telangiectasia, 12(3) HUM. MOL. GENET. 227–32 (2003).) In culture, AT cells are also checkpoint-deficient compared to normal cells. AT cells fail to show an increase in p53 protein levels after treatment with IR or radiomimetic chemicals. (R. E. Shackelford et al. The Ataxia telangiectasia Gene Product Is Required for Oxidative Stress-induced G1 and G2 Checkpoint Function in Human Fibroblasts, 276(24) J. BIOL. CHEM. 21951–59 (2001).) The G1 and G2 checkpoint defects are evident as reduced delay in cell cycle progression. (M. F. Lavin & Y. Shiloh, The Genetic Defect in Ataxia-telangiectasia, 15 ANNU. REV. IMMUNOL. 177–202 (1997).) Furthermore, DNA damage fails to induce an arrest in DNA synthesis in AT cells.

Genomic instability is of great importance because it may increase predisposition to cancer, as well as promote metastasis through cell cycle abnormalities. Investigators are also studying the potential links between AT genomic instability and premature ageing. (K. K. Wong et al. Telomere Dysfunction and Atm Deficiency Compromises Organ Homeostasis and Accelerates Ageing, 421(6923) NATURE 643–48 (2003).) Despite the growing body of research, including the identification and isolation of ATM, the mutated gene that causes AT, there is no cure for AT. Current modalities for treating AT are directed only toward partially alleviating symptoms. These treatments include physical and occupational therapy to maintain flexibility, speech therapy, and gamma-globulin injections and vitamins to supplement weakened immune systems. At this time, there are no therapies to ameliorate the progression of the disease. Prior art has failed to address the issue of increasing genomic stability to effect treatment of AT. In particular, the prior art has failed to focus on modulating the harmful effects of oxidative stress as a way to increase genomic stability in AT patients as well as the myriad of other disease states in which oxidative stress plays a role.

For these and other reasons there is a need for the present invention.

Accordingly, it is a primary objective of the present invention to provide a method for treating AT and other disease states associated with oxidative stress and/or genomic instability in animals.

It is, therefore, an object of the present invention to provide a method for treating AT by administering to an animal a therapeutically effective amount of a chelating agent and/or and a pharmaceutical carrier and/or an antioxidant to increase genomic stability. The present invention can be employed to treat any disease or disorder characterized by genomic instability.

Another objective of the present invention is to provide a method for treating AT by administering to an animal a therapeutically effective amount of a chelating agent and/or and a pharmaceutical carrier to decrease oxidative stress. The present invention can be employed to treat any disease or disorder characterized by oxidative stress.

It is yet another object of the present invention to provide a method for treating AT by administering to an administering to an animal a therapeutically effective amount of a chelating agent capable of binding transition metals and/or and a pharmaceutical carrier and/or an antioxidant to increase genomic stability and/or decrease oxidative stress.

It is a yet further objective of the present invention to provide a method for treating AT by administering to cells a therapeutically effective amount of a chelating agent and a pharmaceutically acceptable carrier so that genomic stability in said cells is increased compared to cells that were not treated.

It is, therefore, an object of the present invention to provide a method for treating AT by administering to an animal a therapeutically effective amount of a chelating agent and a pharmaceutically acceptable carrier so that oxidative stress in said cells in decreased compared to cells that were not treated.

Accordingly, it is a further objective of the present invention to provide a method for providing a composition for treating AT comprising providing a composition comprising a chelating agent and a pharmaceutically acceptable carrier.

It is another objective of the present invention to provide a method for providing a composition for treating AT comprising providing a composition comprising a chelating agent and a pharmaceutically acceptable carrier and/or an antioxidant.

It is a further objective of the present invention to provide a method for treating AT by administering to an animal a therapeutically effective amount of a chelating agent and a pharmaceutically acceptable carrier and an antioxidant.

It is another objective of the present invention to provide a method for treating AT by administering a therapeutically effective amount of an antioxidant.

It is, therefore, an object of the present invention to provide a method for treating AT by administering to an animal or cells a therapeutically effective amount of a chelating agent and a pharmaceutical carrier and/or an antioxidant to decrease or protect against oxidative stress caused by exogenous sources, including irradiation.

The method and means of accomplishing each of the above objectives as well as others will become apparent from the detailed description of the invention which follows hereafter.

SUMMARY OF THE INVENTION

The present invention describes methods and pharmaceutical compositions for treating diseases or disorders associated with oxidative stress and/or genomic instability. The present invention also provides methods and pharmaceutical compositions for treating ataxia-telangeictasia (AT) and such disease states that are characterized by DNA repair deficiencies, loss of cell cycle checkpoint, and disruption to telomeres by administering a therapeutically effective amount of a chelating agent and/or an antioxidant to increase genomic stability and/or decrease oxidative stress.

DETAILED DESCRIPTION OF THE INVENTION

Figure 1:
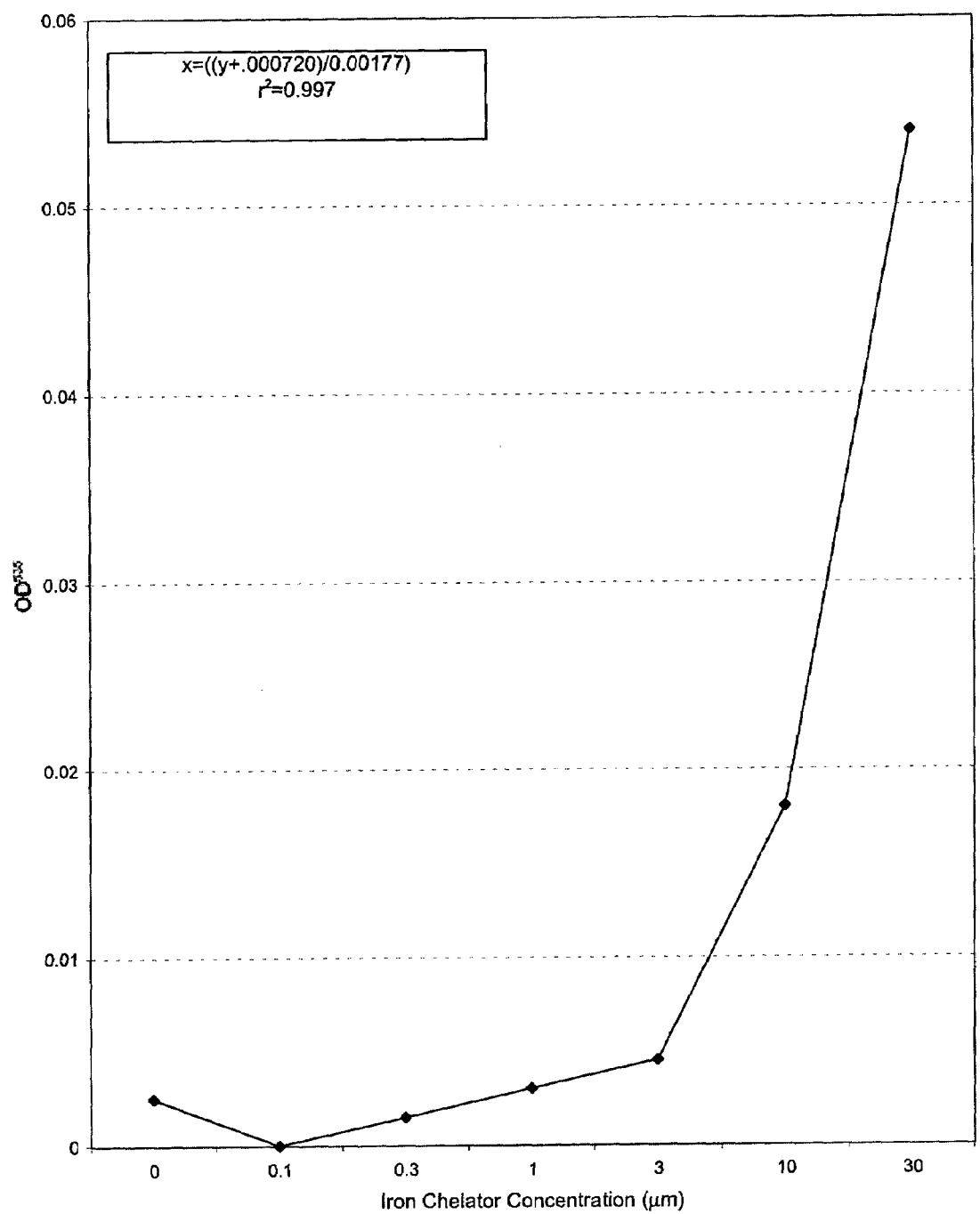
FIG. 1: is a $(NH_4)_2Fe(SO_4)_2$ standard curve via calometric assay to determine the concentration of serum labile ferrous iron in syngeneic normal mice compared to AT mice. AT mice exhibit increase labile serum ferrous iron compared to syngeneic normal mice. Data was analyzed using a student's t-test demonstrating a significant difference between the means of wild-type and AT mouse sera (P=0.013).

Before describing the present invention in detail, it is to be understood that this invention is not limited to the particular treatment regimens, chelating agents, antioxidants, flavonoids, process steps, and materials disclosed herein as such treatment regimens, chelating agents, antioxidants, flavonoids, process steps, and materials may vary. It is also to be understood that the terminology employed herein is used for the purpose of describing particular embodiments only and is not intended to be limiting.

Definitions

As used herein, "effective amount" means an amount of a composition according to the present invention that is nontoxic but sufficient to provide the selected local or systemic effect and performance at a reasonable benefit to risk ratio attending any product of this nature.

A "therapeutically effective amount" refers to the amount of an agent sufficient to induce a desired biological result, i.e., treatment of AT or increase in genomic stability or decrease in oxidative stress. That result may be alleviation of the signs, symptoms, or causes of a disease, or any other desired alteration of a biological system. The amount that is "effective" will vary from subject to subject, and it is not always possible to specify an exact "effective amount." However, an appropriate "effective" amount in any individual case may be determined by one of ordinary skill in the art using routine experimentation.

By "pharmaceutically acceptable," such as in the recitation of a "pharmaceutically acceptable chelating agent," is meant a compound that is not biologically or otherwise undesirable, i.e., the chelating agent that may be administered to a patient/mammal without causing any undesirable biological effects or interacting in a deleterious manner.

A "chelating agent" refers to a substance, compound, mixture, or formulation capable of having an affinity for iron, copper or other transition metal and which is capable of binding iron or copper or any other transition metal in vitro or in vivo. When used in this invention, the chelating agent is useful in chelating/binding ferrous iron or copper or other transition metal and/or decreasing oxidative stress by acting as a transition metal sequestrant and/or antioxidant.

As used herein, the term "antioxidant" refers to synthetic or natural substances that prevent or delay oxidative stress.

Flavonoids are phenolic compounds that typically possess fifteen carbon atoms; two benzene rings joined by a linear three carbon chain. Typically, a "flavonoid" includes any of a class of polyphenolic molecules (including hesperetin and derivatives thereof) based on a flavan nucleus, comprising 15 carbon atoms, arranged in three rings as $C_6$—$C_3$—$C_6$. Flavonoids are generally classified into subclasses by the state of oxidation and the substitution pattern at the C2–C3 unit. New flavonoids are being discovered at a rapid pace. Currently, more than 20,000 have been identified in nature, from sources including vegetables, berries, fruits, wine and beer, or alternately synthesized. Flavonoids as described herein refer to antioxidant activity and/or free radical-scavenging abilities. Furthermore, the term "flavonoid" encompasses, but are not limited to, flavanones, flavonols, flavones, anthocyanidins, chalcones, dihydrochalcones, aurones, flavanols, dihydroflavanols, proanthocyanidins (flavan-3,4-diols), isoflavones and neoflavones.

"Transition metals" as described herein refer to herein includes the 38 elements in groups 3 through 12 of the periodic table, having valence electrons that can be present in more than one shell allowing them to exhibit several common oxidation states. Transition metals include the following: copper, manganese, nickel, cobalt, iron, cadmium, scandium, titanium, vanadium, chromium, zinc, yttrium, zirconium, niobium, molybdenum, technetium, ruthenium, rhodium, palladium, silver, hafnium, tantalum, tungsten, rhenium, osmium, iridium, platinum, gold, mercury, rutherfordium, dubnium, seaborgium, bohrium, hassium, meitnerium, ununnilium, unununium, ununbium.

The terms "treating" and "treatment" as used herein refer to any treatment of AT or other disease or disorder characterized by genomic instability that is treatable by administering to an animal a chelating agent that reduces the severity and/or frequency of symptoms, eliminates symptoms and/or their underlying cause, prevents the occurrence of symptoms and/or their underlying cause, and mitigates damage. The present method of "treating" a clinically symptomatic individual/animal in an individual in need of treatment thereof, as the term is used herein, thus encompasses both increasing genomic stability and/or inhibiting or protecting against genomic instability, e.g., arresting or slowing its development as quantified in assays which measure results of injury such as death and inhibition of metabolic activity; these can be measured, for example, using appropriate fluorescent dyes or measuring enzyme activity. Appropriate viability assays include but are not limited to MTT assays, mitotic index assays, see Cellomics, Inc., Pittsburgh, DNA synthesis assays, as determined by the incorporation of 3H-thymidine, or fluorescence activated cell sorting (FACS) or enzyme linked immunosorbent assays (ELISA), or plating assays, including limiting dilution assays and colony growth assays that measure the reproductive integrity of the surviving cells as well as the plating efficiency. The present method of "treating" a clinically symptomatic individual/mammal in an individual in need of treatment thereof, as the term is used herein, also encompasses both decreasing oxidative stress and/or inhibiting or protecting against oxidative stress, e.g., arresting or slowing its development, as quantified in assays which measure results of injury such as death and inhibition of metabolic activity; these can be measured, for example, using appropriate fluorescent dyes or measuring enzyme activity.

AT cells refer to cells from individuals diagnosed with AT or expressing ATM.

In general, the present invention is directed to methods for treating AT by administering a therapeutically effective amount of a pharmaceutically acceptable chelating agent and/or antioxidant to increase genomic stability and/or decrease oxidative stress. The present invention can be employed to treat any disease or disorder characterized by genomic instability.

Examples of diseases or disorders characterized by genomic instability include but are not limited to Bloom's syndrome (BS), Nijmegen Breakage syndrome (NBS), and Werner syndromes (WS) Fanconi anemia (FA), xeroderma pigmentosum (XP), Rothmund_Thomson Syndrome (RTS), Cockayne Syndrome (CS), Hereditary Nonpolyposis Colorectal Cancer (HNPCC), Cowden Syndrome, pPTEN, and the Multiple Hamartoma Syndromes, Familial Pancreatic Cancer, Familial Breast Cancer and BRCA1/2, Multiple Endocrine Neoplasia, MEN1 and RET, Malignantmelanoma, CMM, CDKN2 and CDK4, Neurofibromatosis and NF1/2, Nevoid basal Cell Carcinoma Syndrome (Gorlin's Syndrome) and PTCH, Renal Cell Carcinoma, Retinoblastoma and Rb, Von Hippel-Lindau Disease and VHL.

Further, the present invention is intended for use in the treatment of all types of diseases and disorders characterized by oxidative stress.

As noted above, oxidative stress is a pathological phenomenon which also appears to be responsible for a large number of other conditions in AT. By oxidative stress is meant the stress on the living cell through accumulation of toxic oxidized compounds, such as lipid hydroperoxides, hydrogen peroxide, singlet oxygen and hydroxyl/superoxide anions. It is moreover possible for the stress to arise through free radicals which are produced locally or supplied from outside, especially so-called reactive oxygen species (ROS) or peroxonitrite free radicals etc. The oxidative stress can also be induced, for example, by exposure to radiation, xenobiotics, heavy metal ions or ischemia/reperfusion.

Examples of diseases or disorders characterized by oxidative stress include but are not limited to aging, cancer, arthritis, cardiovascular disease, Alzheimer's disease, and diabetes.

Prior to this invention, it was not realized in the art that chelating agents and/or flavonoids/antioxidants could be used for treating AT. The inventors herein have discovered the utility of a method for treating AT. The method involves generally the use of chelating agents and/or antioxidants which the present inventors have found provides a surprising and remarkable ability to specifically decrease oxidative stress and to increase genome stability in AT cells. Further, applicant has surprisingly discovered that oxidative stress is decreased and genomic stability is increased in AT cells with and without exogenous oxidative stress.

Figure 2:
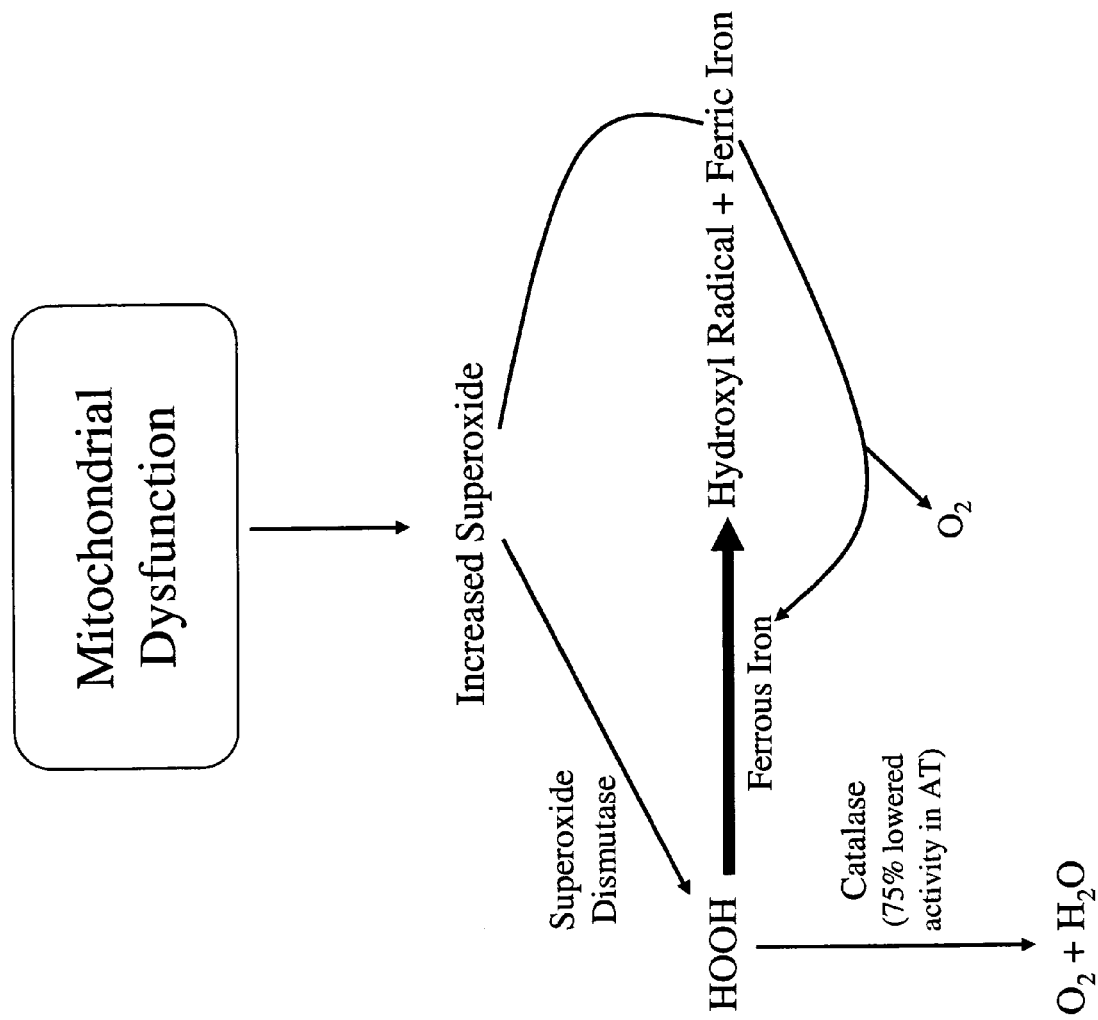
FIG. 2: is a model of possible ferrous iron activity and subsequent redox reactions in AT cells. Mitochondrial dysfunction leads to increased superoxide, which becomes hydrogen peroxide (HOOH) via cellular superoxide dismutase (SOD) activity. Lowered catalase activity (seen in AT, see D. Watters et al. Localization of a Portion of Extranuclear ATM to Peroxisomes, J. BIOL. CHEM. 274, 34277–34282 (1999)), results in an increased pool of HOOH, which in turn becomes the toxic hydroxyl radical via the presence of ferrous iron acting as a Fenton catalyst (bold arrow). The ferric iron that results from the Fenton chemistry may be regenerated to ferrous iron via reduction from the increased superoxide level found in AT (See K. L. Quick, & L. L. Dugan, Superoxide Stress Identifies Neurons at Risk in a Model of Ataxia-telangiectasia, 49 ANN NEUROL. 627–635 (2001).)

The invention relates to the discovery that the AT mice have elevated levels of labile ferrous iron (labile iron). (FIG. 1). Although this invention is not limited to any particular theory or mechanism, new evidence indicates that AT is in part, a disease of dysregulated redox metabolism where labile iron and/or copper may be dysregulated in AT and its chelation by various chelating agents increases the genomic stability of AT cells via labile iron and/or copper sequestration, resulting in lowered Fenton chemistry activity, concomitant lowered hydroxyl radical production and a net increase in genomic stability and cell survival. (A. Barzilai et al. ATM Deficiency and Oxidative Stress: a New Dimension of Defective Response to DNA Damage, 1 DNA REPAIR 3–25 (2002).) (FIG. 2).

Although chelating agents are described in further detail in a previous section, the method of the invention may be achieved using any chelating agent specific for a transition metal administered in a therapeutically effective amount.

Therapeutic Chelating Agents Suitable for Use in Methods of the Invention

In one embodiment, the invention relates to a method for treating AT by administering a therapeutically effective amount of a pharmaceutically acceptable chelating agent or antioxidant to increase genomic stability.

In a further embodiment, a therapeutic chelating agent includes any one or more of transition metal chelating agent or a pharmaceutically acceptable chelating agent thereof.

In another embodiment, a therapeutic chelating agent includes any one or more of ferrous iron chelating agents, e.g., ferrioxamine, trihydroxamic acid, CP94, EDTA, desferrioxamine hydroxamic acids, deferoxamine B (DFO) as the methanesulfonate salt, also known as desferrioxamine B mesylate (DFOM), desferal from Novartis (previously Ciba-Giegy), apoferritin, CDTA (trans-1,2-diaminocyclohexane-N,N,N',N'-tetraacetic acid), and DTPA (diethylenetriamine-N,N,N',N'',N''-penta-acetic acid), or a pharmaceutically acceptable chelating agent thereof.

In yet another embodiment, as an addition or as an alternative to therapeutic chelating agents that solely bind iron, the therapeutic chelating agent may also be capable of binding copper or another transition metal as well.

In another embodiment, a therapeutic chelating agent includes any one or more of copper chelating agents, e.g., penecillamine, triene, bathocuproine disulfonate, diethylenetriamine pentaacetic acid, or a pharmaceutically acceptable chelating agent thereof.

While chelating agents that can cross cell membranes are the preferred chelating agents for use in this invention, such as desferrioxamine, other chelating agents, such as DPTA are also suitable.

In one embodiment, the ferrous iron chelating agent DPTA is used to increase the genomic stability of AT cells.

In another embodiment, the ferrous iron chelating agent desferroxiamine is used to increase the genomic stability of AT cells. (FIGS. 3–7).

In yet another embodiment, the ferrous iron chelating agent desferal is used to increase the genomic stability of AT cells.

In still another embodiment, the ferrous iron chelating agent apoferritin is used to increase the genomic stability of AT cells. (FIGS. 8A–9C).

In an alternate embodiment, the copper chelating agent penecillamine is used to increase the genomic stability of AT cells.

In an additional embodiment, the chelating agent that is able to bind two or more transition metals, such as iron and copper, is used to increase the genomic stability of AT cells.

While chelating agents can increase genomic stability in AT cells, antioxidants may also be suitable for increasing genomic stability.

In still another embodiment, antioxidants are selected from the group of flavonoids, such as quercetin, morin, naringenin and hesperetin, taxifolin, afzelin, quercitrin, myricitrin, genistein, apigenin and biochanin A.

Figure 10A:
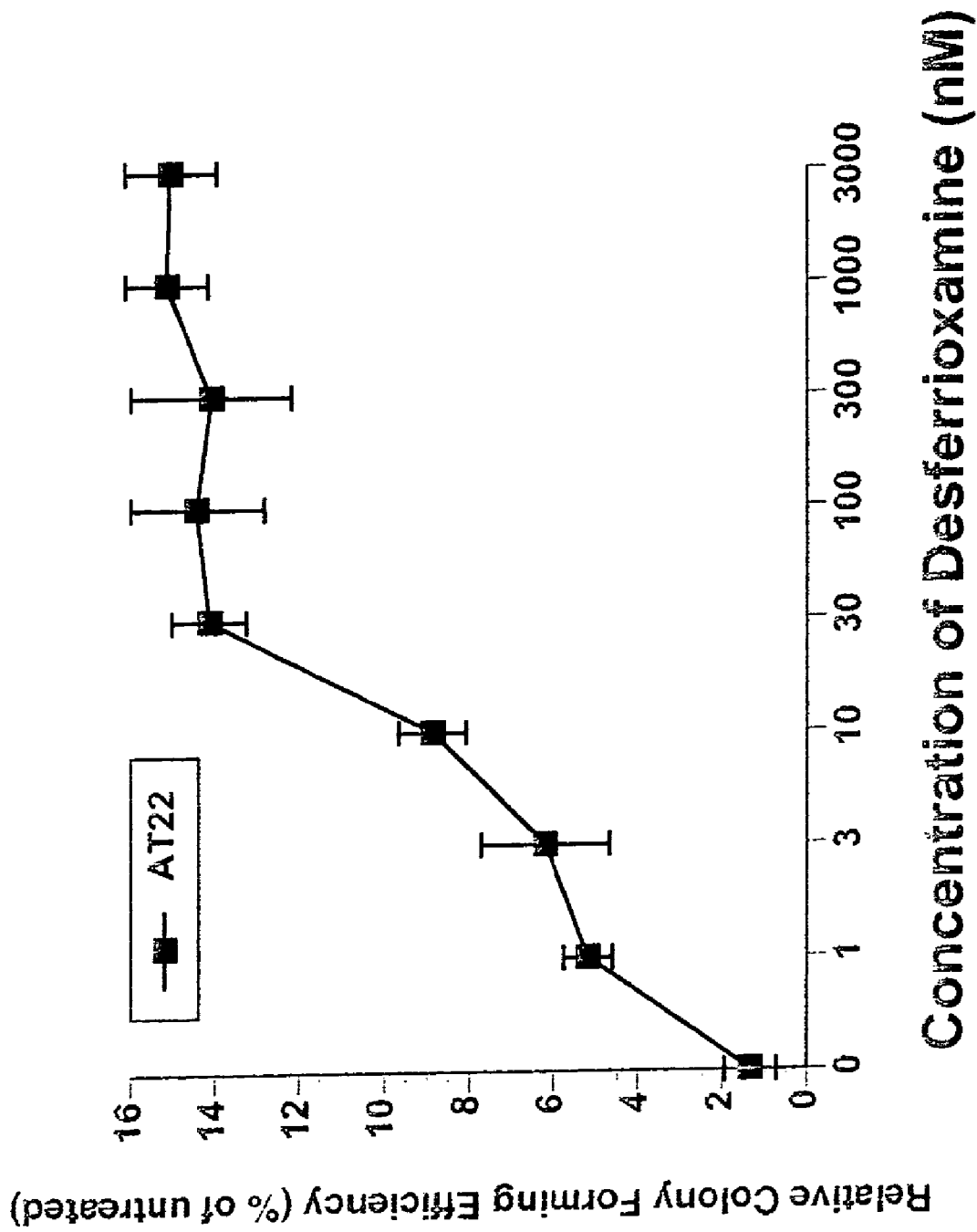
FIG. 10A: is a standard curve showing cell survival data of AT22 cells treated with increasing concentrations of desferrioxamine then subjected to t-BOOH toxicity. The results are expressed as a percentage of the survival of untreated cells as measured using a colony forming-efficiency assay. Increasing concentrations of desferrioxamine and aspirin increase the resistance of AT22 cells to the toxic effects of t-BOOH in the colony forming-efficiency assay. Abbreviations in figure legends; Asp, aspirin; Def, desferrioxamine.]
Figure 10B:
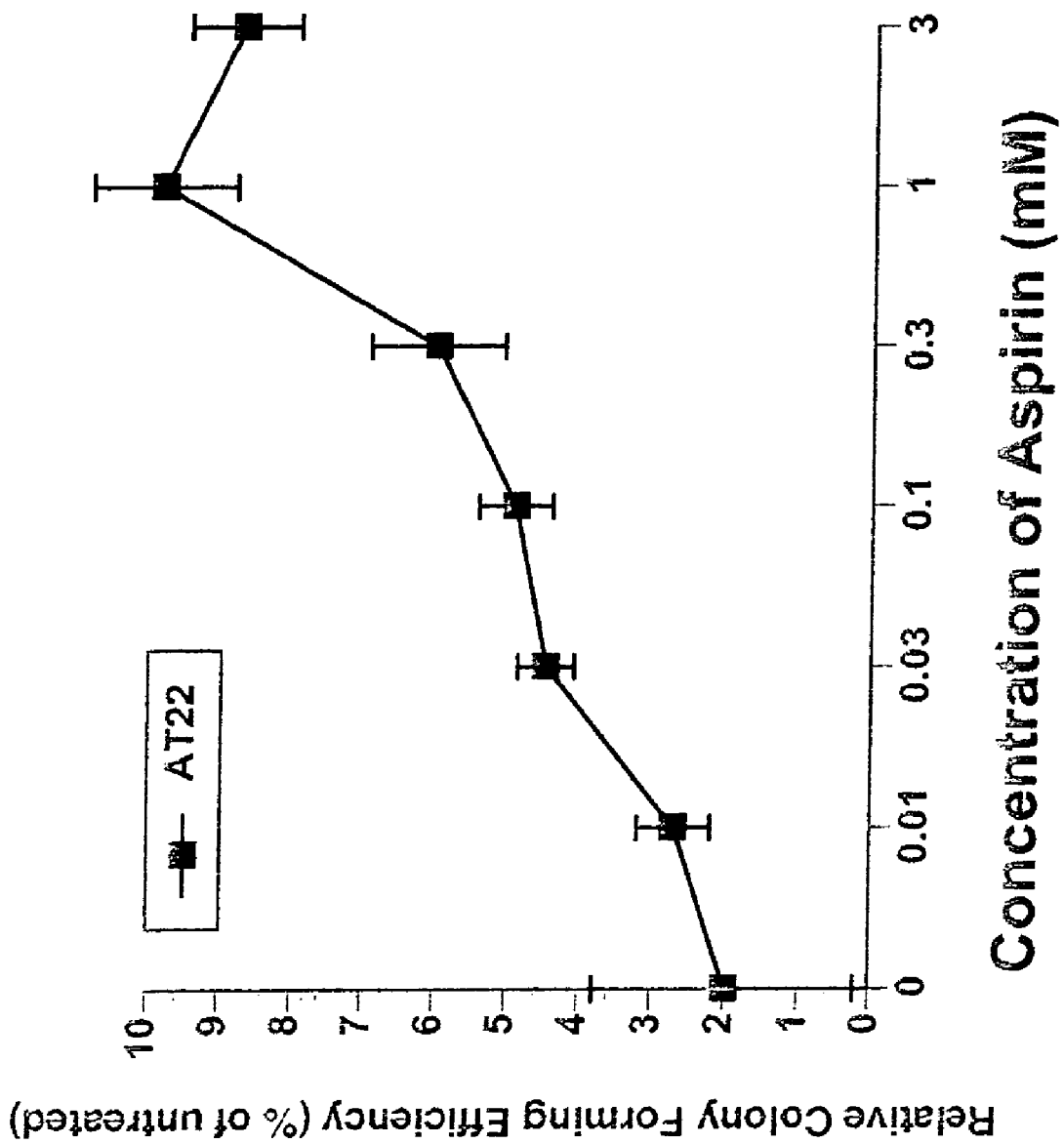
FIG. 10B: is a standard curve showing cell survival data of AT22 cells treated with increasing concentrations of aspirin then subjected to t-BOOH toxicity. The results are expressed as a percentage of the survival of untreated cells as measured using a colony forming-efficiency assay. Abbreviations in figure legends; Asp, aspirin; Def, desferrioxamine.]

In a further embodiment, the flavonoid quercetin is used to increase the genomic stability of AT cells. (FIGS. 10A–B).

Figure 11A:
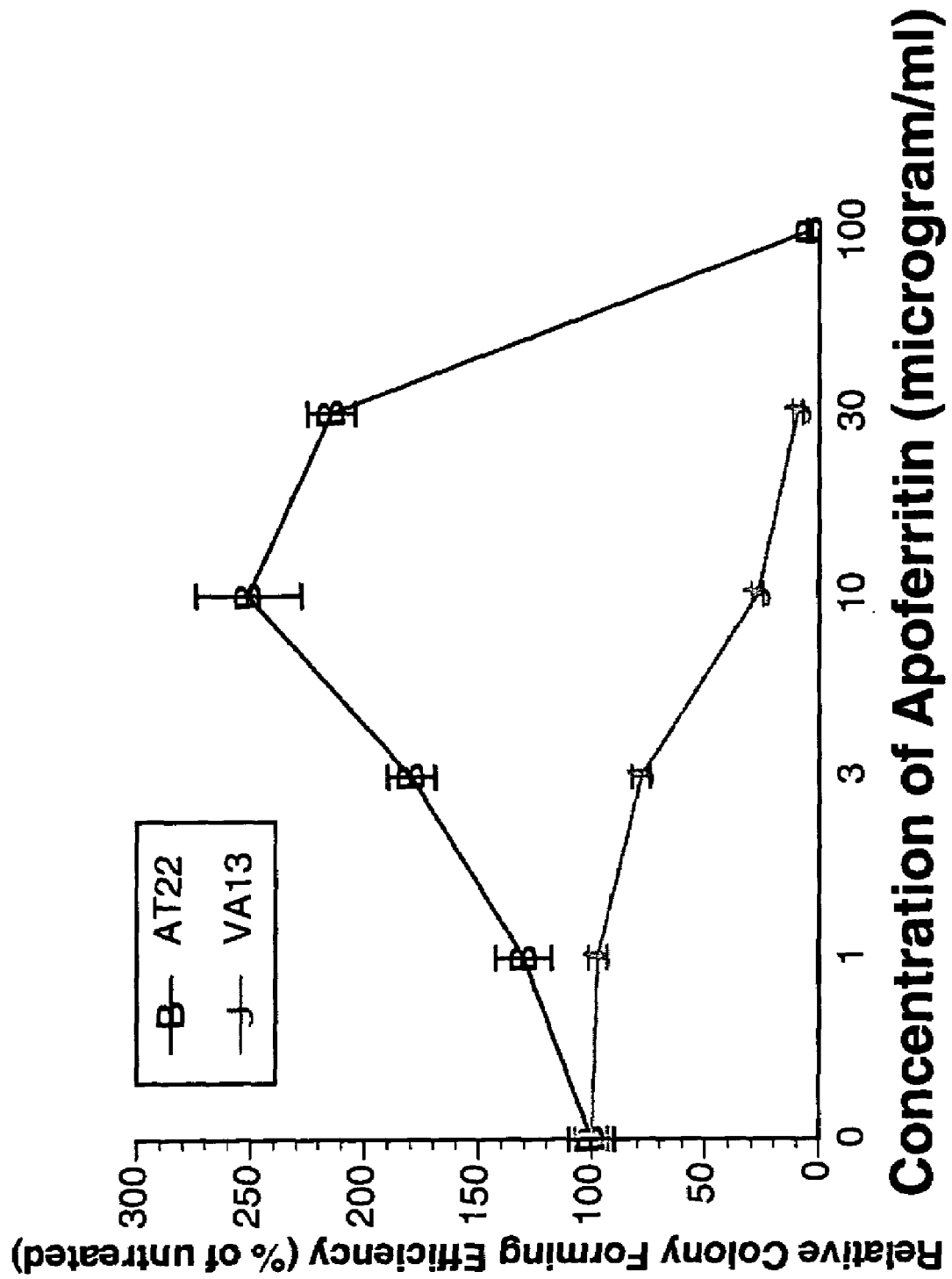
FIG. 11A: is a standard curve showing cell survival data of VA13, NHF1, AT22, ATDM-1, and ATDM-2 cells treated with increasing concentrations of apoferritin. The results are expressed as a percentage of the survival of untreated cells as measured using a colony forming-efficiency assay. Long-term culture with apoferritin increases the plating efficiency of AT cells in the colony forming-efficiency assay.
Figure 11B:
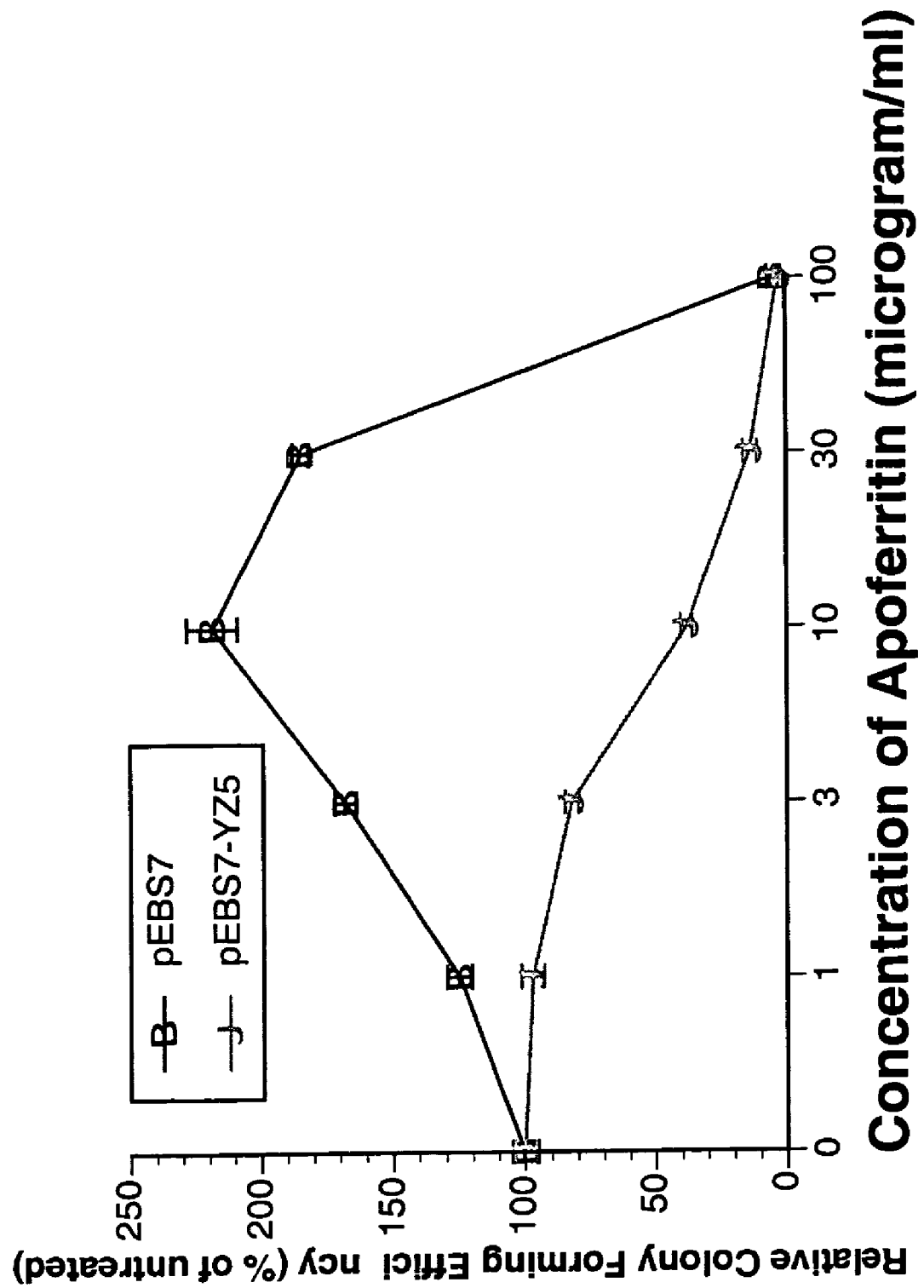
FIG. 11B: is a standard curve showing cell survival data of pEBS7-YZ5 cell lines treated with increasing concentrations of apoferritin, pEBS7 (pATM deficient) cells used for comparison. The results are expressed as a percentage of the survival of untreated cells as measured using a colony forming-efficiency assay.
Figure 12A:
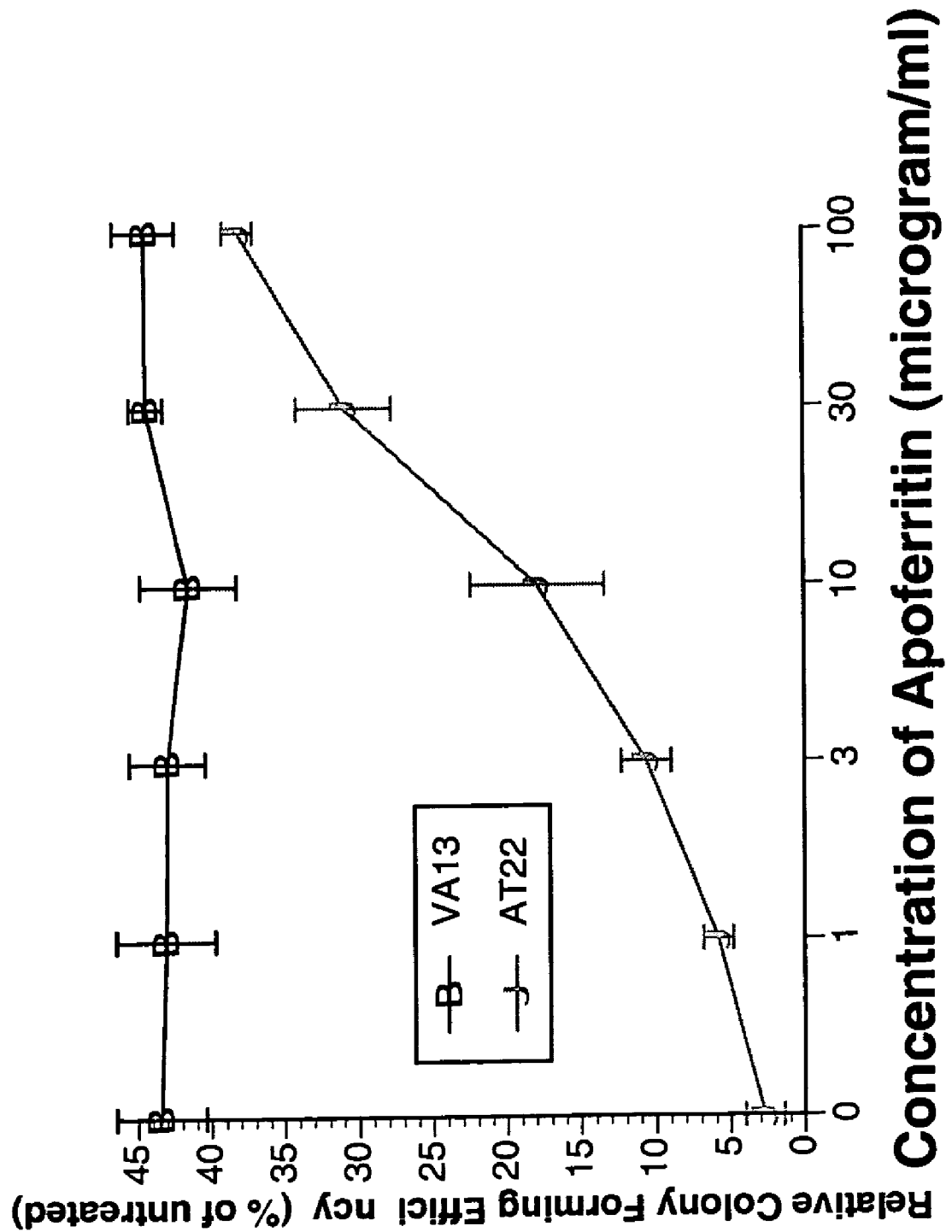
FIG. 12A: is a standard curve showing cell survival data of AT22 and VA13 cells pretreated with increasing concentrations of apoferritin then subjected to t-BOOH toxicity. The results are expressed as a percentage of the survival of untreated cells as measured using a colony forming-efficiency assay. Pretreatment of AT and normal cells with apoferritin results in increased resistance to t-BOOH toxicity in the colony forming-efficiency assay.
Figure 12B:
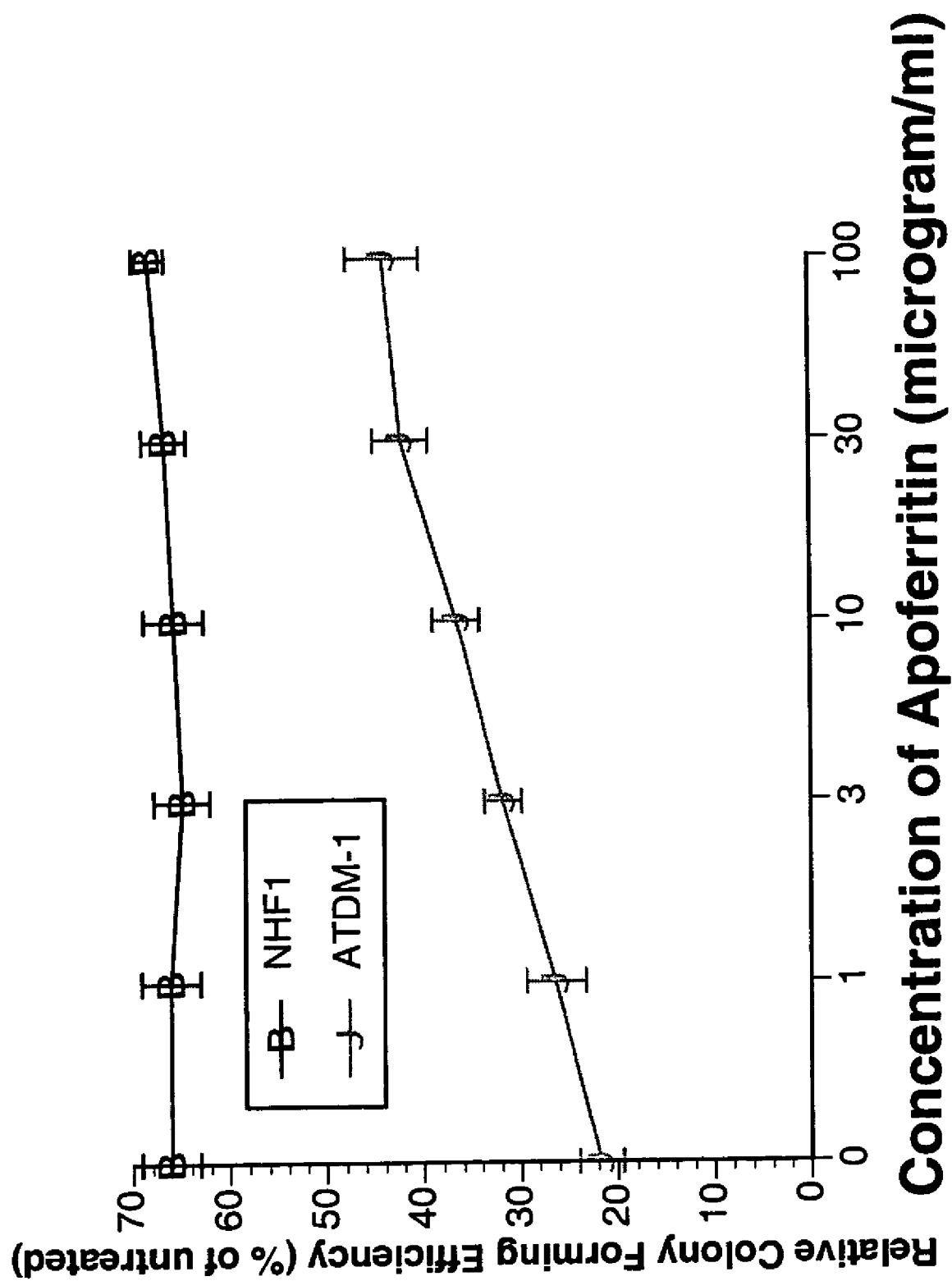
FIG. 12B: is a standard curve showing cell survival data of ATDM-1 cells pretreated with increasing concentrations of apoferritin then subjected to t-BOOH toxicity. NHF1 cells were used as a normal cell control. The results are expressed as a percentage of the survival of untreated cells as measured using a colony forming-efficiency assay.
Figure 12C:
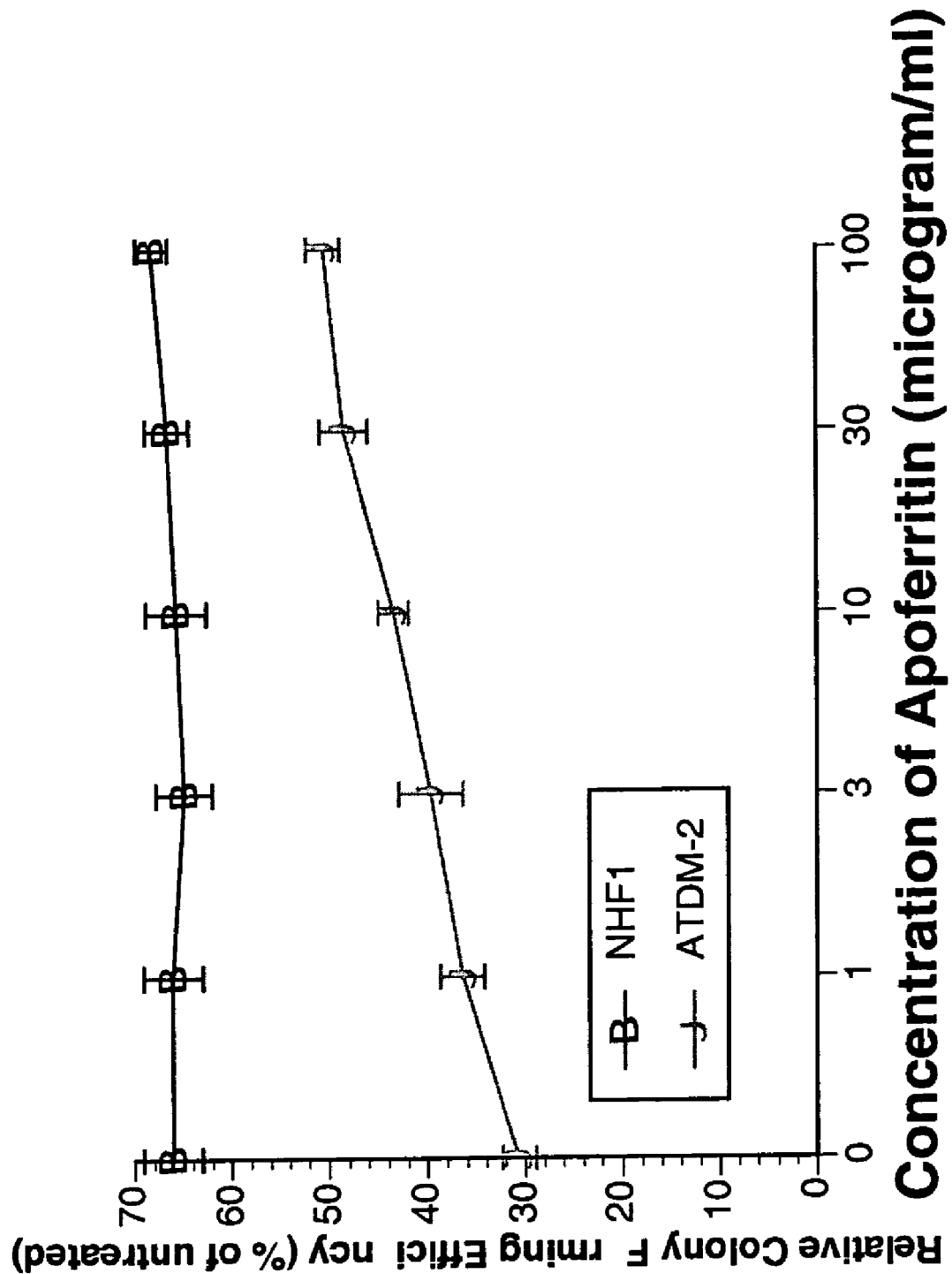
FIG. 12C: is a standard curve showing cell survival data of ATDM-2 cells pretreated with increasing concentrations of apoferritin then subjected to t-BOOH toxicity. NHF1 cells were used as a normal cell control. The results are expressed as a percentage of the survival of untreated cells as measured using a colony forming-efficiency assay.
Figure 13A:
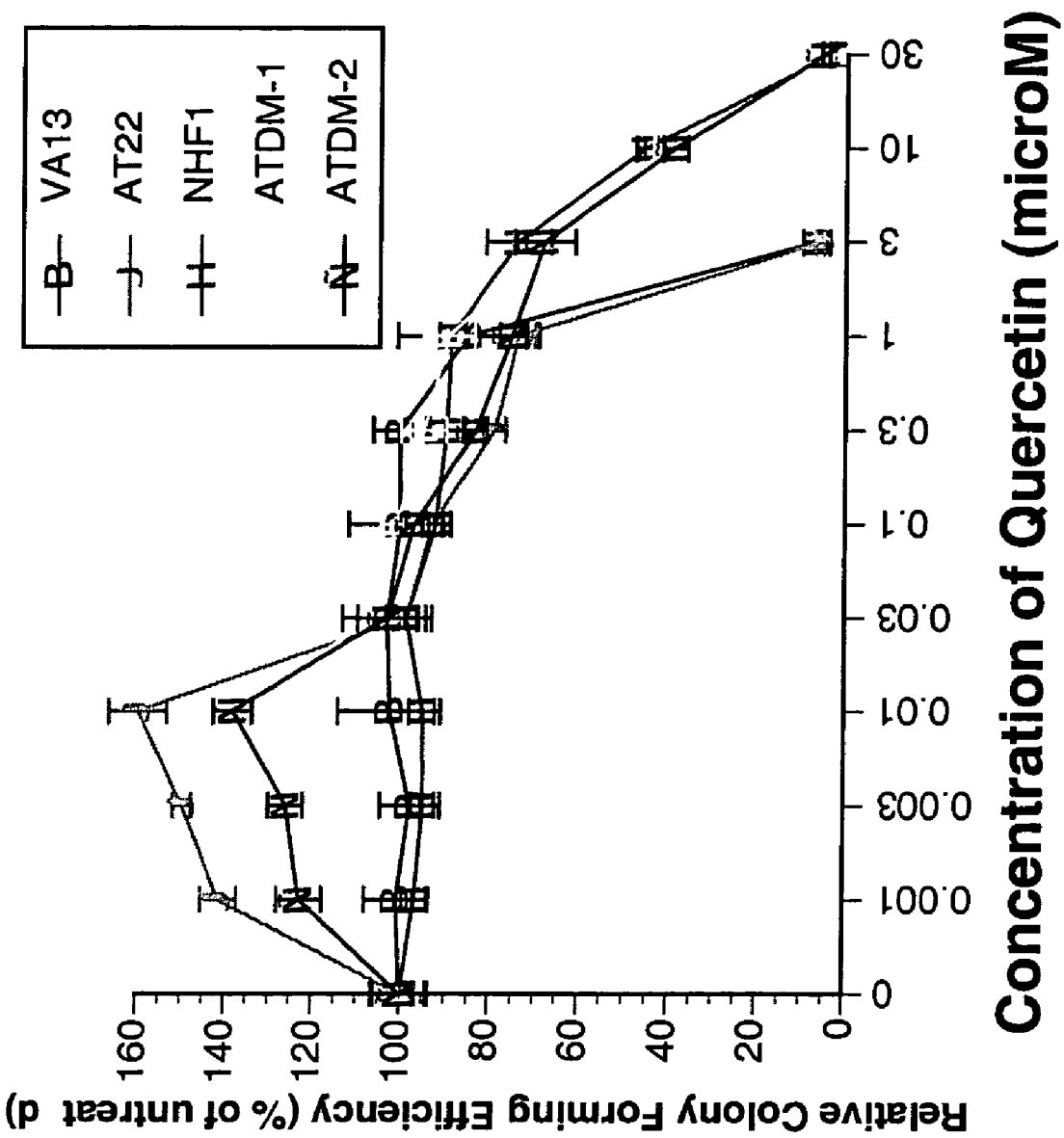
FIG. 13A: is a standard curve showing cell survival data of VA13, NHF1, AT22, ATDM-1, and ATDM-2 cells treated with increasing concentrations of quercetin, The results are expressed as a percentage of the survival of untreated cells as measured using a colony forming-efficiency assay. Long-term culture with quercetin increases the plating efficiency of AT cells in the colony forming-efficiency assay.
Figure 13B:
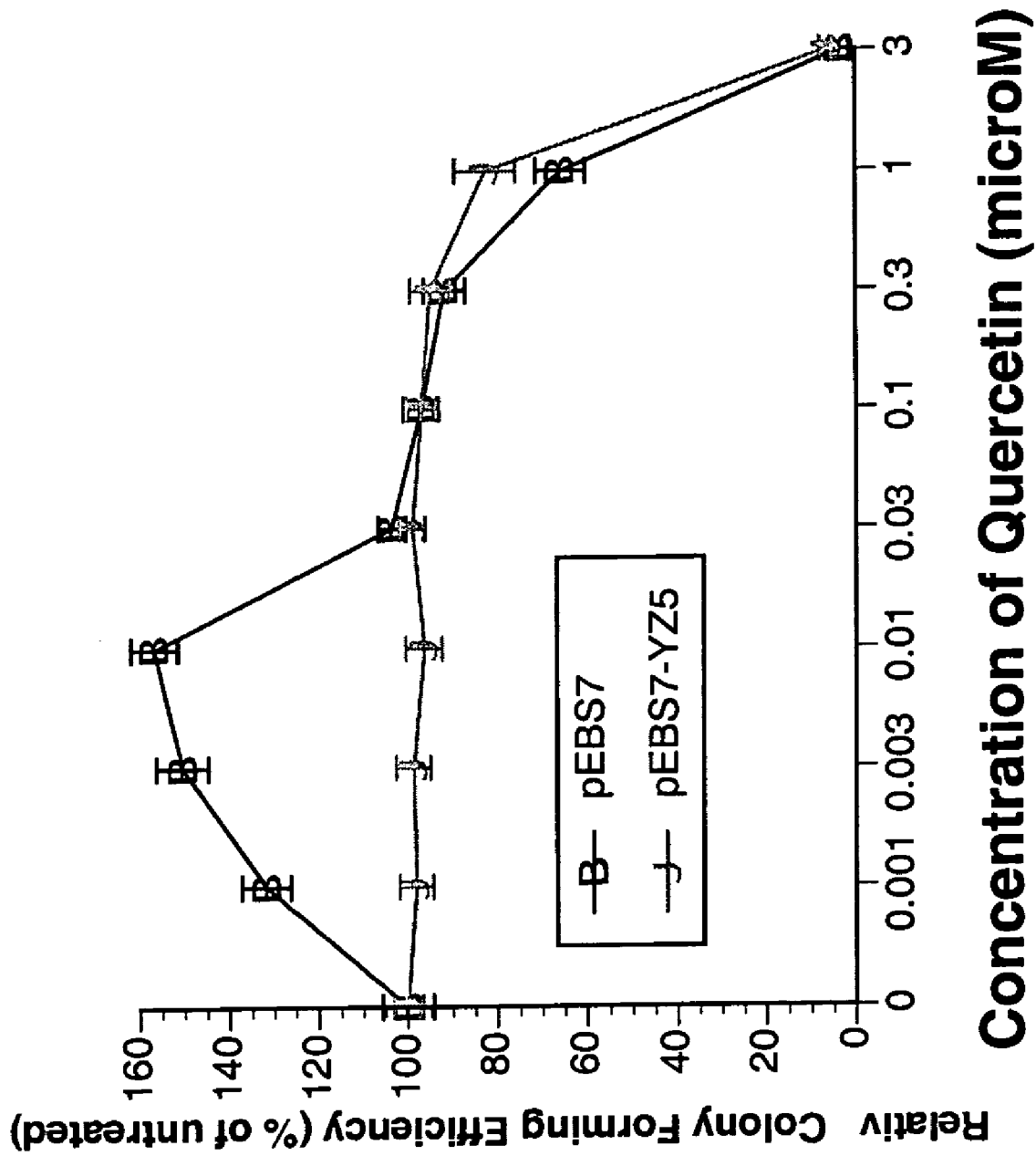
FIG. 13B: is a standard curve showing cell survival data of pEBS7-YZ5 cells treated with increasing concentrations of quercetin; pEBS7 (pATM deficient) cells used for comparison. The results are expressed as a percentage of the survival of untreated cells as measured using a colony forming-efficiency assay.
Figure 14A:
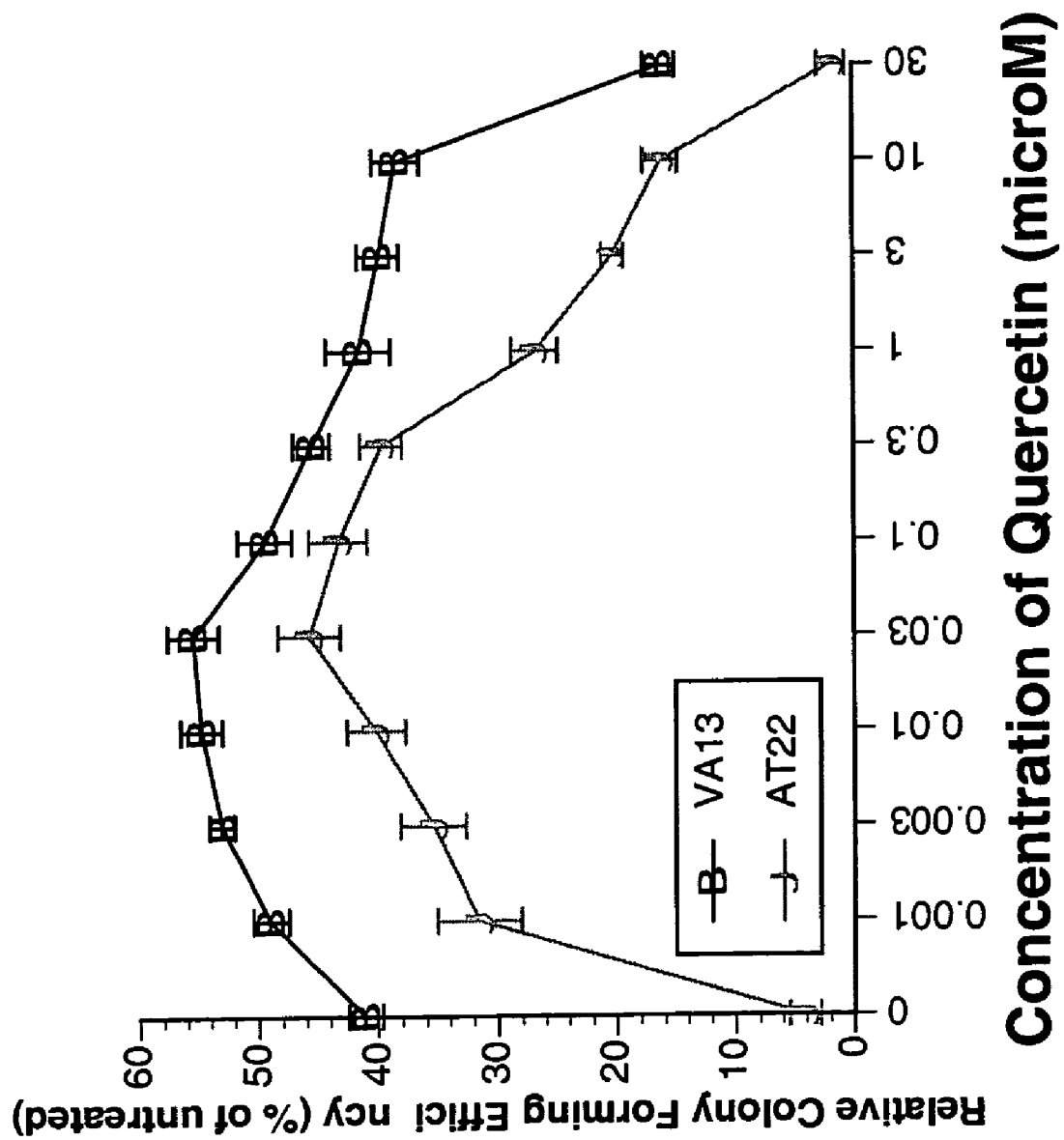
FIG. 14A: is a standard curve showing cell survival data of AT22 and VA13 cells pretreated with increasing concentrations of quercetin then subjected to t-BOOH toxicity. The results are expressed as a percentage of the survival of untreated cells as measured using a colony forming-efficiency assay. Pretreatment of AT and normal cells with quercetin results in increased resistance to t-BOOH toxicity in the colony forming-efficiency assay.
Figure 14B:
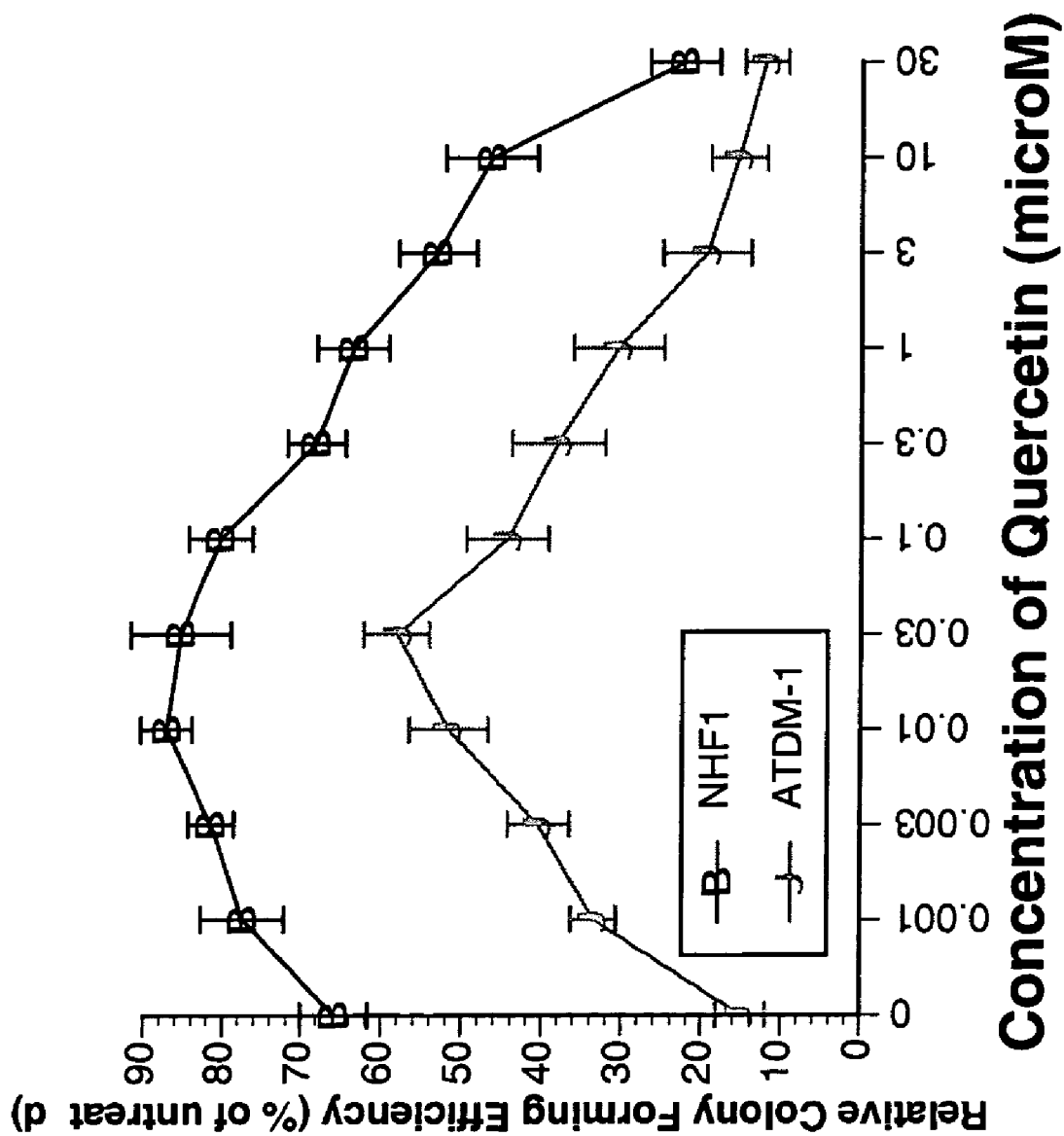
FIG. 14B: is a standard curve showing cell survival data of ATDM-1 and NHF1 cells pretreated with increasing concentrations of quercetin then subjected to t-BOOH toxicity. The results are expressed as a percentage of the survival of untreated cells as measured using a colony forming-efficiency assay.
Figure 14C:
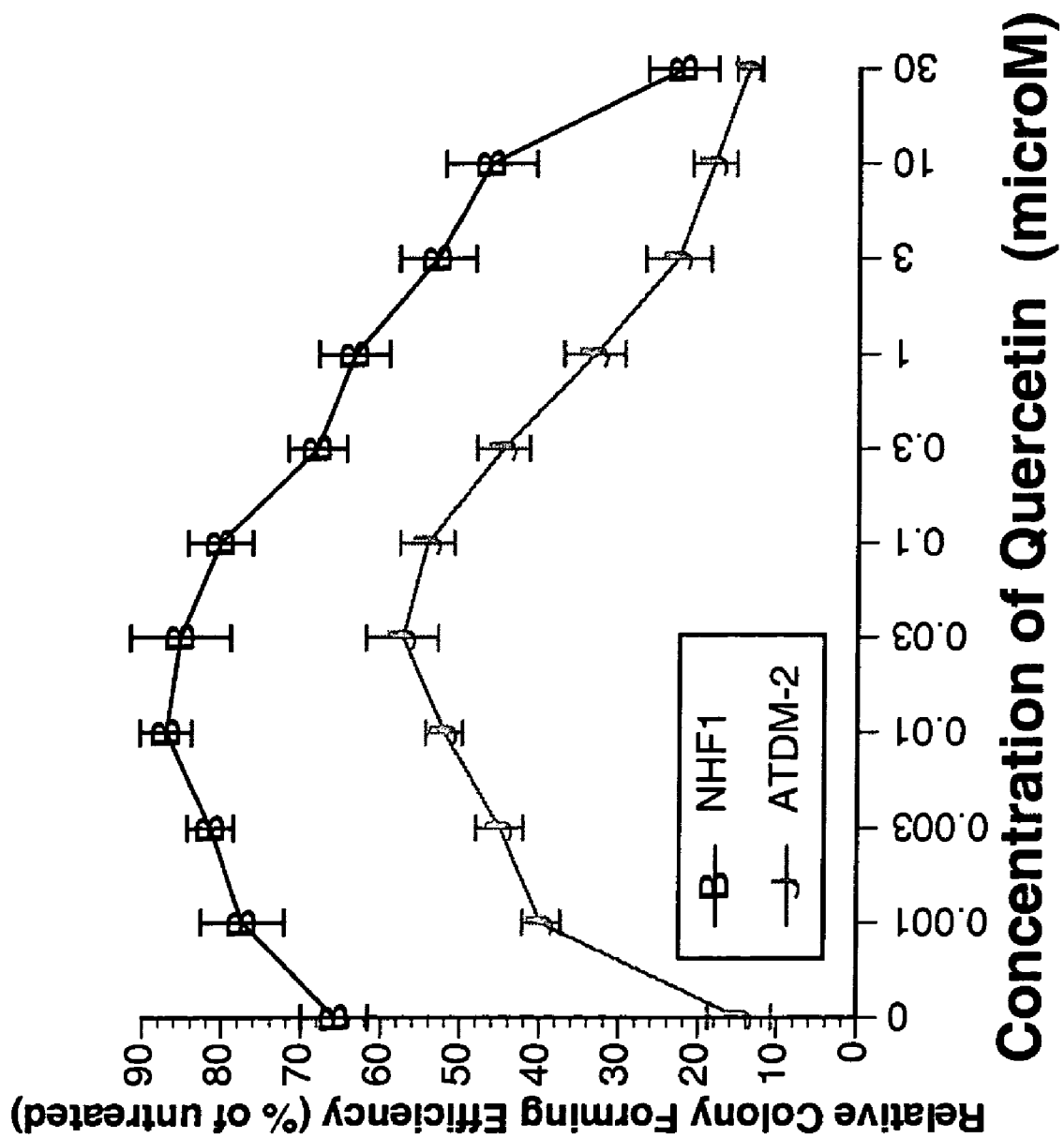
FIG. 14C: is a standard curve showing cell survival data of ATDM-2 and NHF1 cells pretreated with increasing concentrations of quercetin then subjected to t-BOOH toxicity. The results are expressed as a percentage of the survival of untreated cells as measured using a colony forming-efficiency assay.

In yet another alternate embodiment, the flavonoid quercetin is used to increase the genomic stability of AT cells under oxidative stress. (FIGS. 11A–C).

In still another alternate embodiment, the flavonoid quercetin is used to increase the genomic stability of AT cells under oxidative stress from the presence of t-butyl hydroperoxide (t-BOOH). (FIGS. 11A–C).

In an alternate embodiment, a substance that induces a chelating agent to bind a transition metal such as iron or copper is used to increase the genomic stability of AT cells.

In yet another alternate embodiment, aspirin is used to increase the genomic stability of AT cells. (FIGS. 8A–9, 10B).

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains. The practice of the present invention will employ, unless otherwise indicated, conventional techniques of pharmacotherapy and molecular biology and the like, which are within the skill of the art. Such techniques are fully explained in the literature. See JOSEPH SAMBROOK, T. MANIATIS, E. F. FRITSCH, MOLECULAR CLONING: A LABORATORY MANUAL (2nd ed., Cold Spring Harbor Lab. Press, Plainview, N.Y. 1989). CURRENT PROTOCOLS IN CELL BIOLOGY, (J. S. Bonifacino, M. Dasso, J. Lippincott-Schwartz, J. B. Harford, and K. M. Yamada (Editors), John Wiley & Sons, Inc.).

The publications and other material used herein to illuminate the background of the invention or provide additional details respecting the practice, are herein incorporated by reference in their entirety, and for convenience are respectively grouped in the appended Reference.

EXAMPLES

Example 1

Preparation of Cells

AT22, an SV40-transformed skin fibroblast cell line, was obtained from David Cortez at the Baylor Medical School. VA13, an SV40-transformed normal fetal lung fibroblast cell line, was obtained from ATCC (Rockville, Md., USA). pEBS7 and pEBS7-YZ5 tumor cell lines were a generous gift from Dr. Yosif Shiloh at the Sacker School of Medicine, Tel Aviv University, Israel (See Y. Ziv et al. 15 Recombinant ATM Protein Complements the Cellular A-T Phenotype, ONCOGENE 159–167 (1997).). The NHF1 normal foreskin human fibroblast primary cell strain was a generous gift from Richard Pales at the National Institute of Environmental Health Sciences. The primary dermal AT fibroblast cells strains ATDM-1 and ATDM-2 were obtained by skin biopsy from two males, ages 10 and 14, diagnosed with AT and previously demonstrated to lack pATM expression, see FIG. 15, Example 3. The AT22 and VA13 cells lines were cultured in DEEM containing 5% FRS and 1% penicillin/streptomycin/glutamine. The pEBS7 and pEBS7-YZ5 cell lines were grown in the same media with hygromycin at 100 mg/ml (See Y. Ziv et al. 15 Recombinant ATM Protein Complements the Cellular A-T Phenotype, ONCOGENE 159–167 (1997).). The primary fibroblast cell strains were grown in the same media with 20% FCS plus 1% penicillin/streptomycin/glutamine.

Colony Forming-Efficiency Assay

Colony forming-efficiency experiments were performed as previously described (See R. E. Shackelford et al. The Ataxia telangiectasia Gene Product Is Required for Oxidative Stress-induced G1 and G2 Checkpoint Function in Human Fibroblasts, 276 J. BIOL. CHEM. 21951-21959 (2001)). In brief, exponentially growing cells were plated at 2,000 cells/100 mm tissue culture dish in 10 ml appropriate media, allowed to adhere 6 h, and treated 15 min with varying concentrations of t-BOOH or $FeCl_2$ $FeCl_2$, aspirin, diethylenetriaminepentaacetic acid (DTPA), hygromycin, and desferrioxamine mesylate were obtained from Sigma Chemical Corp (St. Louis, Mo.). Fetal calf serum (FCS) and Dulbecco's Modified Eagle's Medium (DMEM) were obtained from Invitrogen (Rockville, Md.). Culture dishes were obtained from Becton Dickinson (Franklin Lakes, N.J.).

Following treatment, the pates were washed 2× with media, the media replaced, and colonies fixed and stained after 14 days in culture by water: methanol addition (1:1) containing crystal violet (1 g/L). Colonies consisting of cell clusters containing greater than 50 cells were counted under a dissecting microscope. Unless otherwise noted, where desferrioxamine and/or aspirin pretreatment was employed, the cells were plated in desferrioxamine, aspirin, or desferrioxamine and aspirin, and allowed to adhere for 6 h. The plates were then washed 4× with media and treated with t-BOOH as above. Data indicates survival as a percentage of untreated cells. The AT22 and VA13 tumor cell lines were used at passages 20–40. The primary NHF1, ATDM-1, and ATDM-2 cell strains were used at passages 6–18. pEBS7 and pEBS7-YZ5 cells were used at passages 15–20. All experiments were done at least twice in triplicate. Standard deviations (error bars) were calculated from each experimental data point divided by the mean untreated value and averaged between experiments to obtain the mean standard deviation. (FIGS. 6–10B).

Example 2

Mitotic Delay Assays

Figure 3:
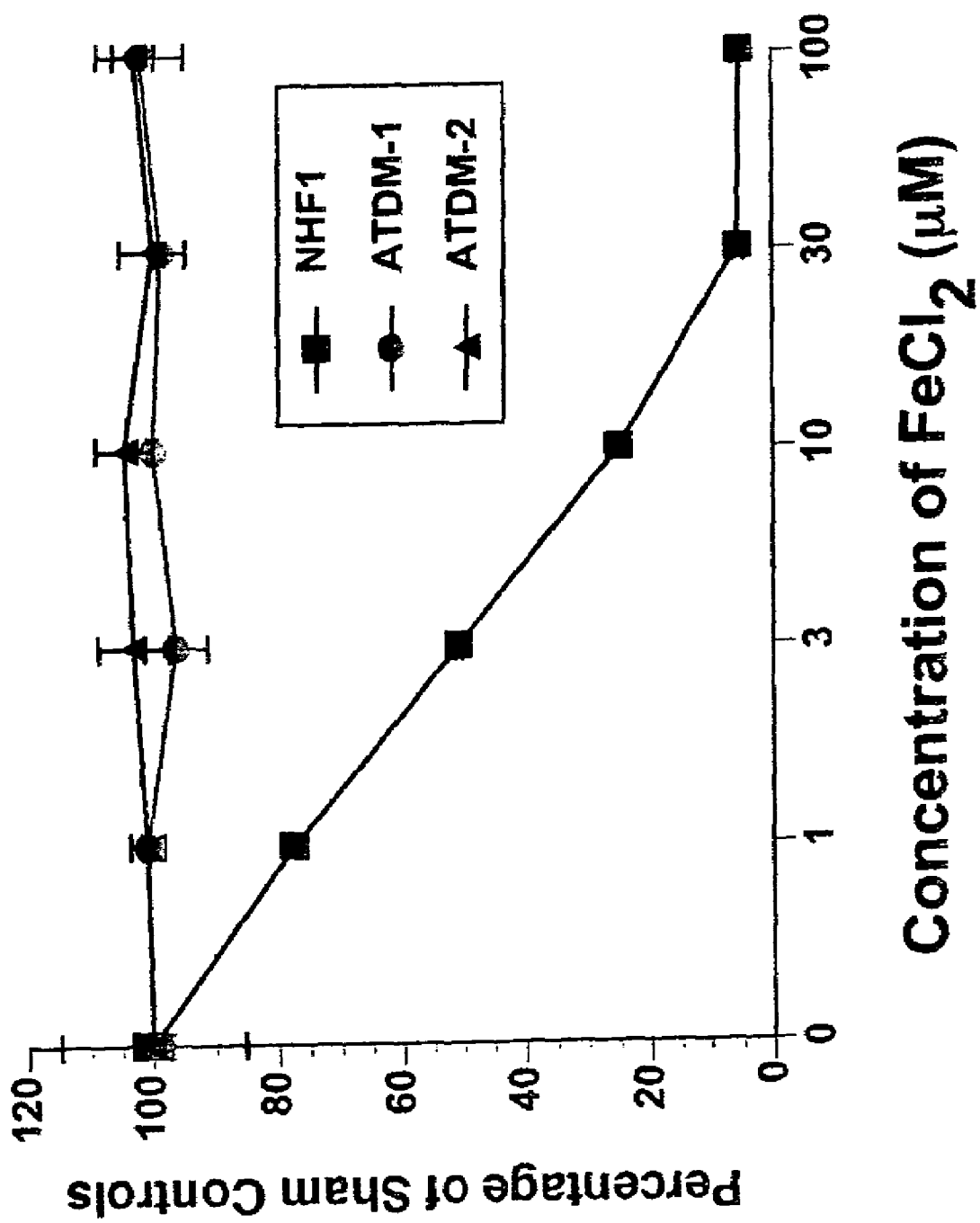
FIG. 3: is a standard curve showing the mitotic activity data of ATDM-1, and ATDM-2 cells when treated with increasing concentrations of $FeCl_2$. NHF1 cells were used for comparison. The results are expressed as a percentage of the mitotic index of the mock-treated population as measured by fluorescence microscopy. $FeCl_2$ induces a pATM-dependent $G_2$ checkpoint.
Figure 4A:
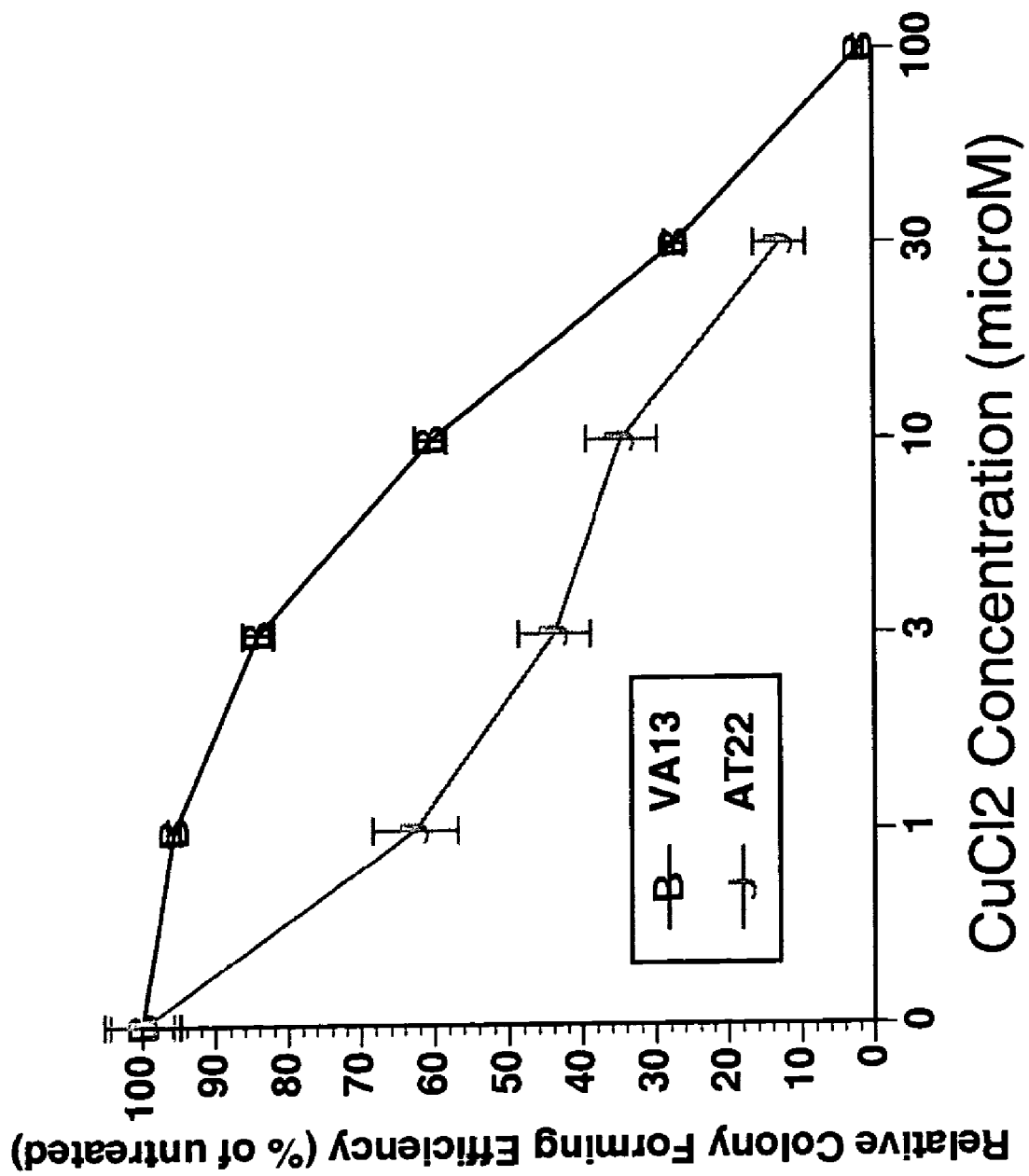
FIG. 4A: is a standard curve showing cell survival data of VA13 and AT22 cells treated with increasing concentrations of $CuCl_2$. The results are expressed as a percentage of the survival of untreated cells as measured using a colony forming-efficiency assay. AT cells exhibit increased sensitivity to $CuCl_2$ in the colony forming-efficiency assay.
Figure 4B:
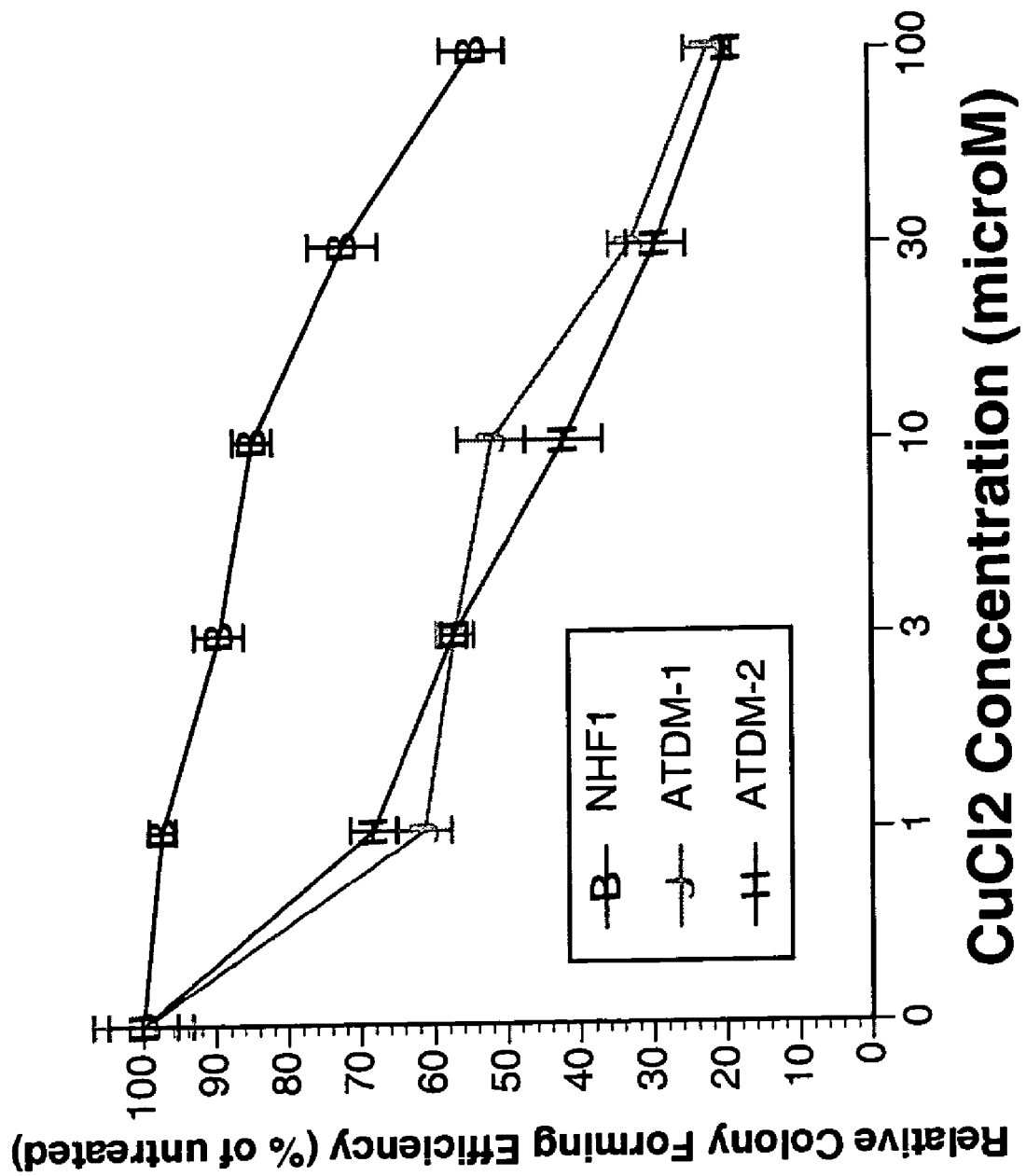
FIG. 4B: is a standard curve showing cell survival data of NHF1, ATDM-1, and ATDM-2 cells treated with increasing concentrations of $CuCl_2$. The results are expressed as a percentage of the survival of untreated cells as measured using a colony forming-efficiency assay.
Figure 5:
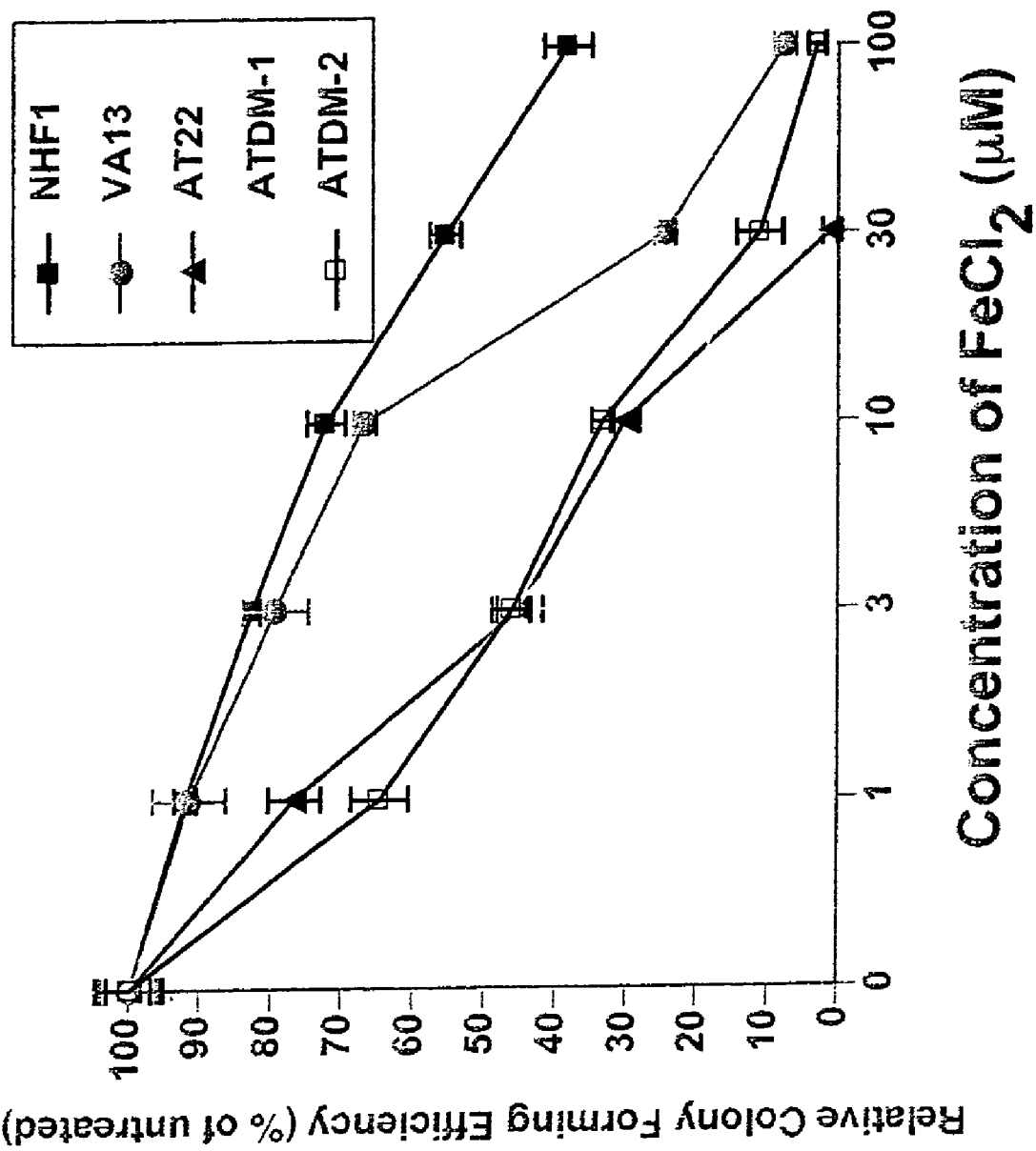
FIG. 5: is a standard curve showing cell survival data of NHF1, VA13, ATDM-1, and ATDM-2 cells treated with $FeCl_2$. The results are expressed as a percentage of the survival of untreated cells as measured using a colony forming-efficiency assay.
Figure 6:
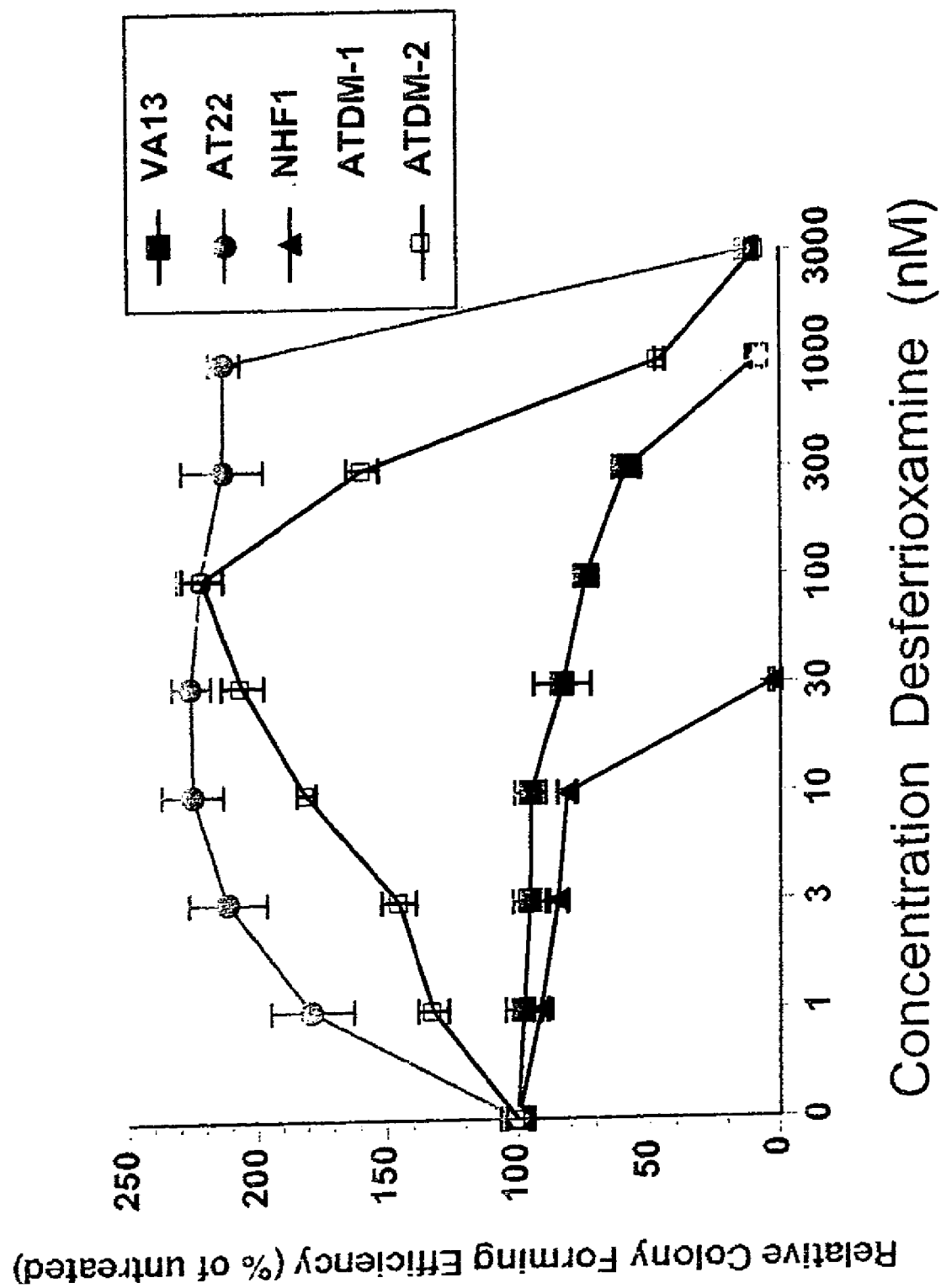
FIG. 6: is a standard curve showing cell survival data of VA 13, NHF1, AT22, ATDM-1, and ATDM-2 cells treated with increasing concentrations of desferrioxamine. The results are expressed as a percentage of the survival of untreated cells as measured using a colony forming-efficiency assay.
Figure 7:
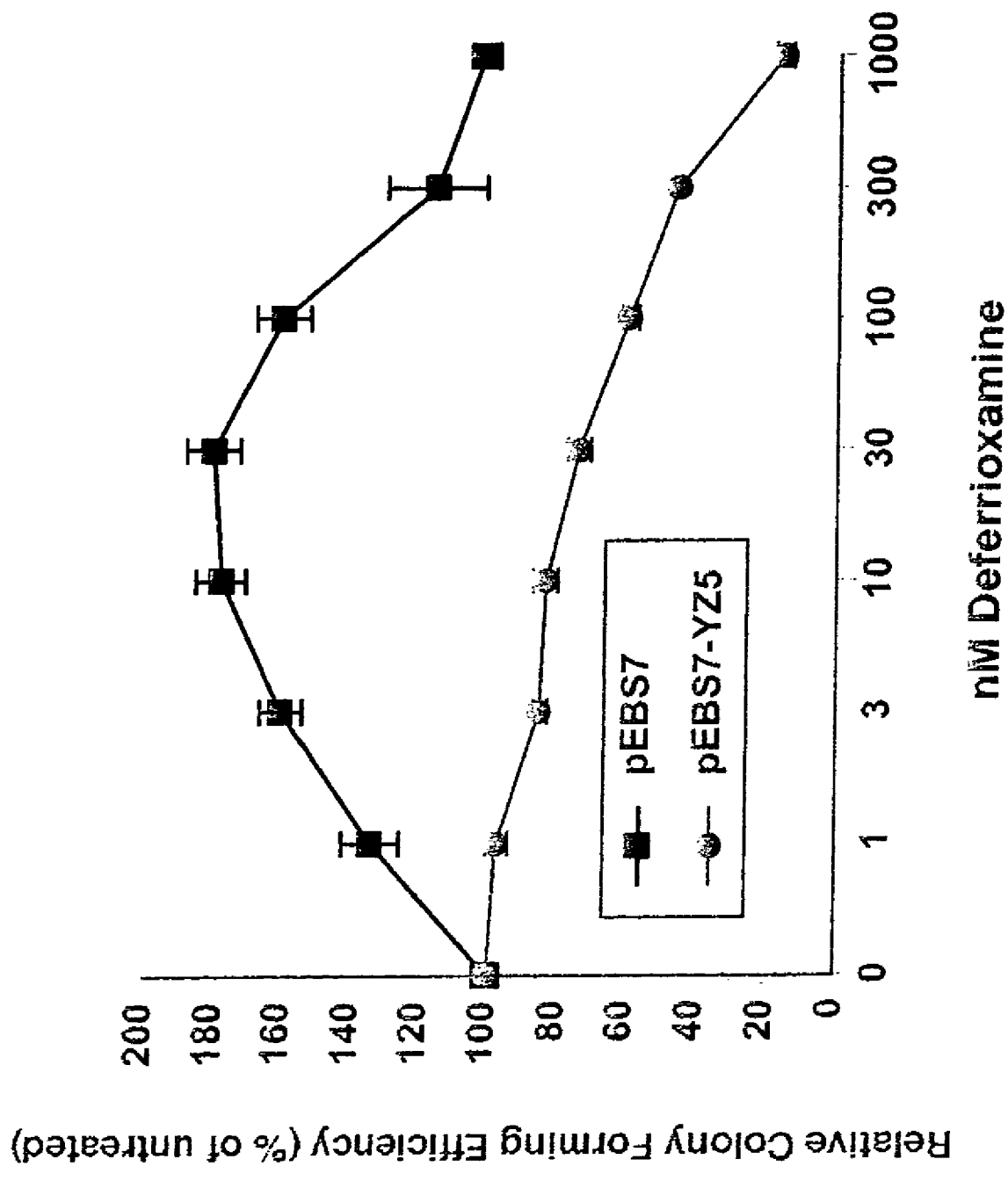
FIG. 7: is a standard curve showing cell survival data of pEBS7-YZ5 (recombinant pATM expressing) and pEBS7 (pATM deficient) cells treated with increasing concentrations of desferrioxamine. The results are expressed as a percentage of the survival of untreated cells as measured using a colony forming-efficiency assay.
Figure 8A:
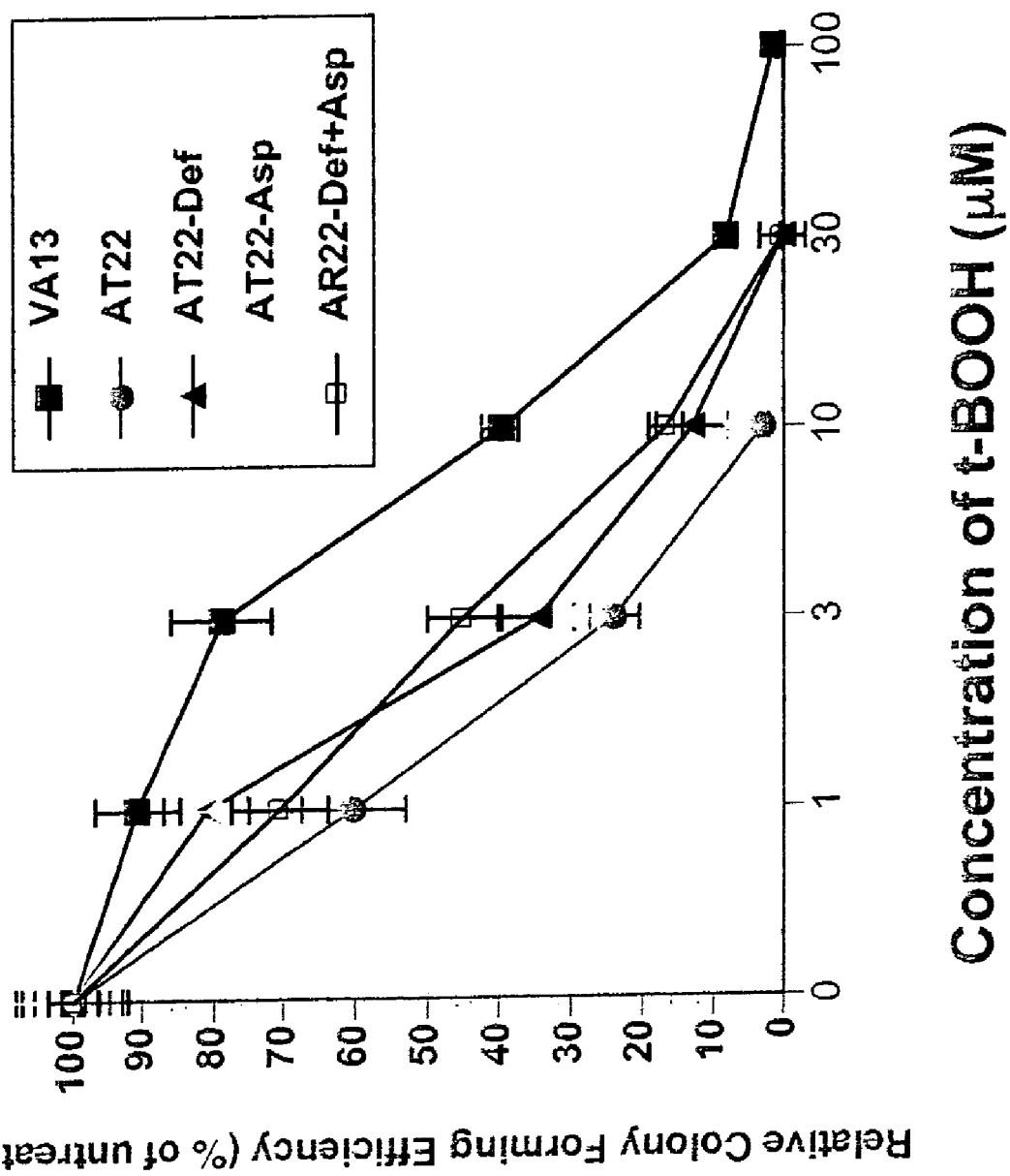
FIG. 8A: is a standard curve showing cell survival data of AT22 and VA13 cells pretreated with desferrioxamine, aspirin or both then subjected to increasing concentrations of t-BOOH toxicity. The results are expressed as a percentage of the survival of untreated cells as measured using a colony forming-efficiency assay. Desferrioxamine and aspirin pretreatment of AT cells results in increased resistance to t-BOOH toxicity in the colony forming-efficiency assay. [Desferrioxamine], 100 µM; [aspirin], 0.3 mM. Abbreviations in figure legend; Asp, aspirin; Def, desferrioxamine.]
Figure 8B:
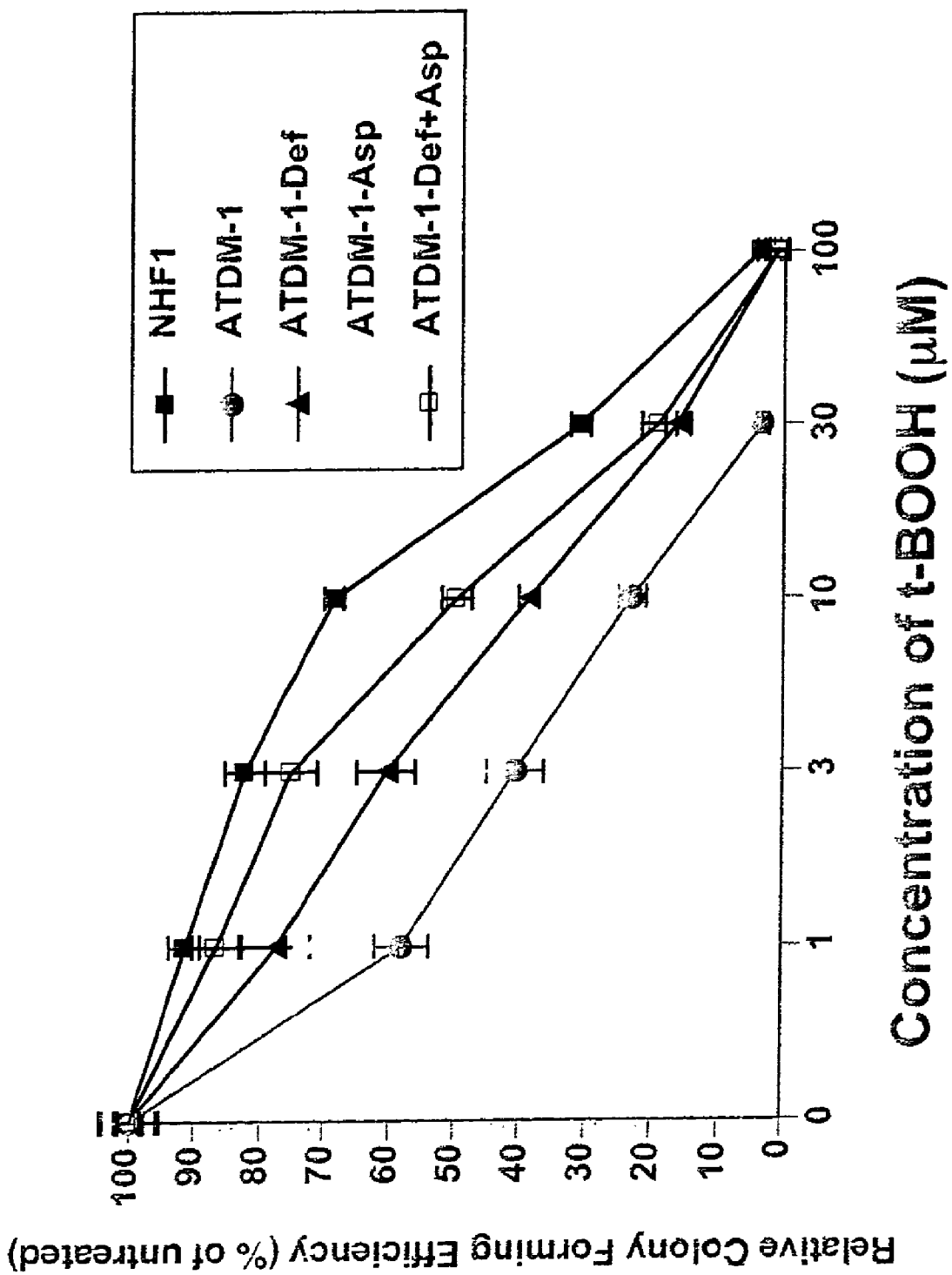
FIG. 8B: is a standard curve showing cell survival data of ATDM-1 and NHF1 cells pretreated with desferrioxamine, aspirin or both then subjected to increasing concentrations of t-BOOH toxicity. The results are expressed as a percentage of the survival of untreated cells as measured using a colony forming-efficiency assay.
Figure 8C:
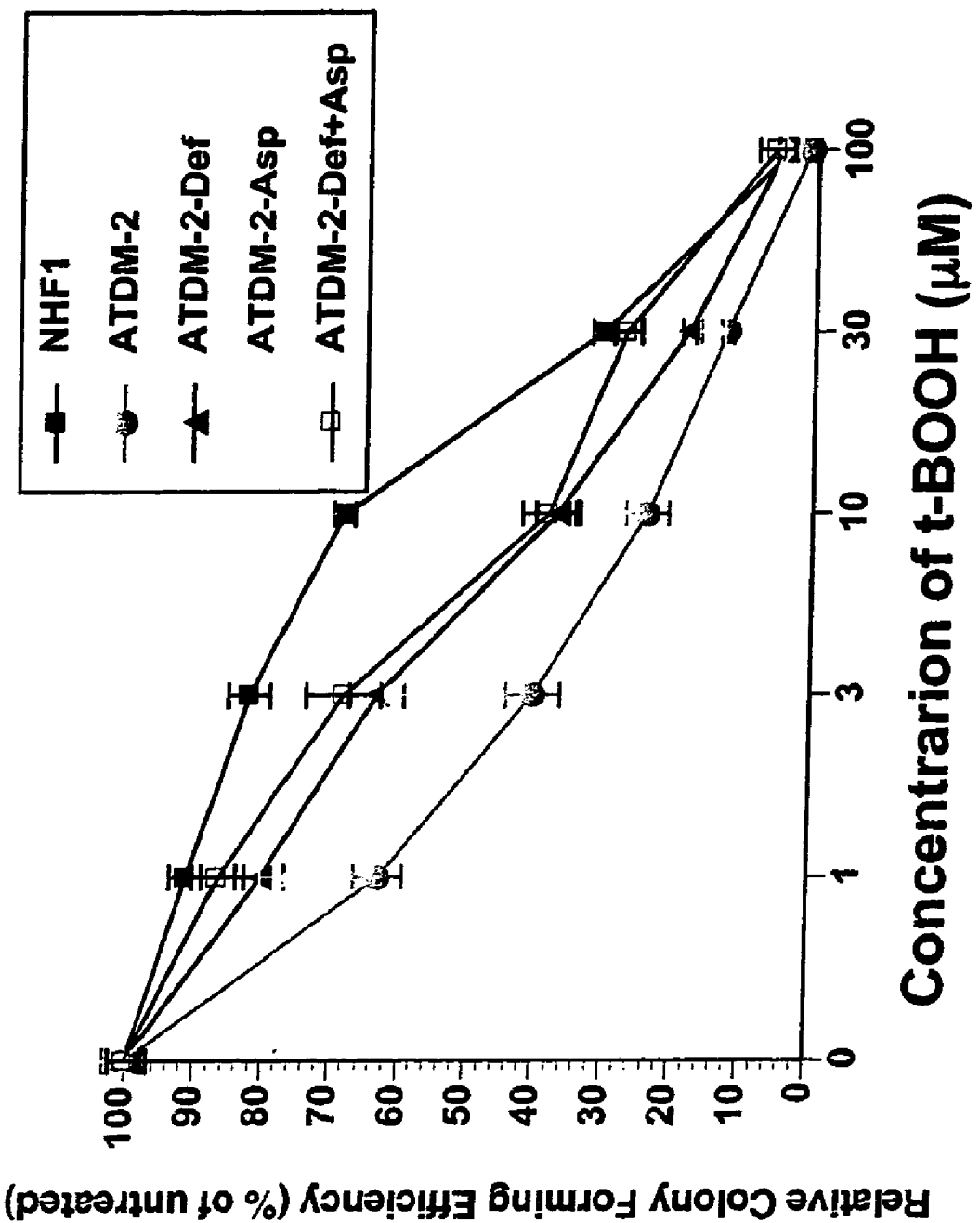
FIG. 8C: is a standard curve showing cell survival data of ATDM-2 and NHF1 cells pretreated with desferrioxamine, aspirin or both then subjected to increasing concentrations of t-BOOH toxicity. The results are expressed as a percentage of the survival of untreated cells as measured using a colony forming-efficiency assay.
Figure 9:
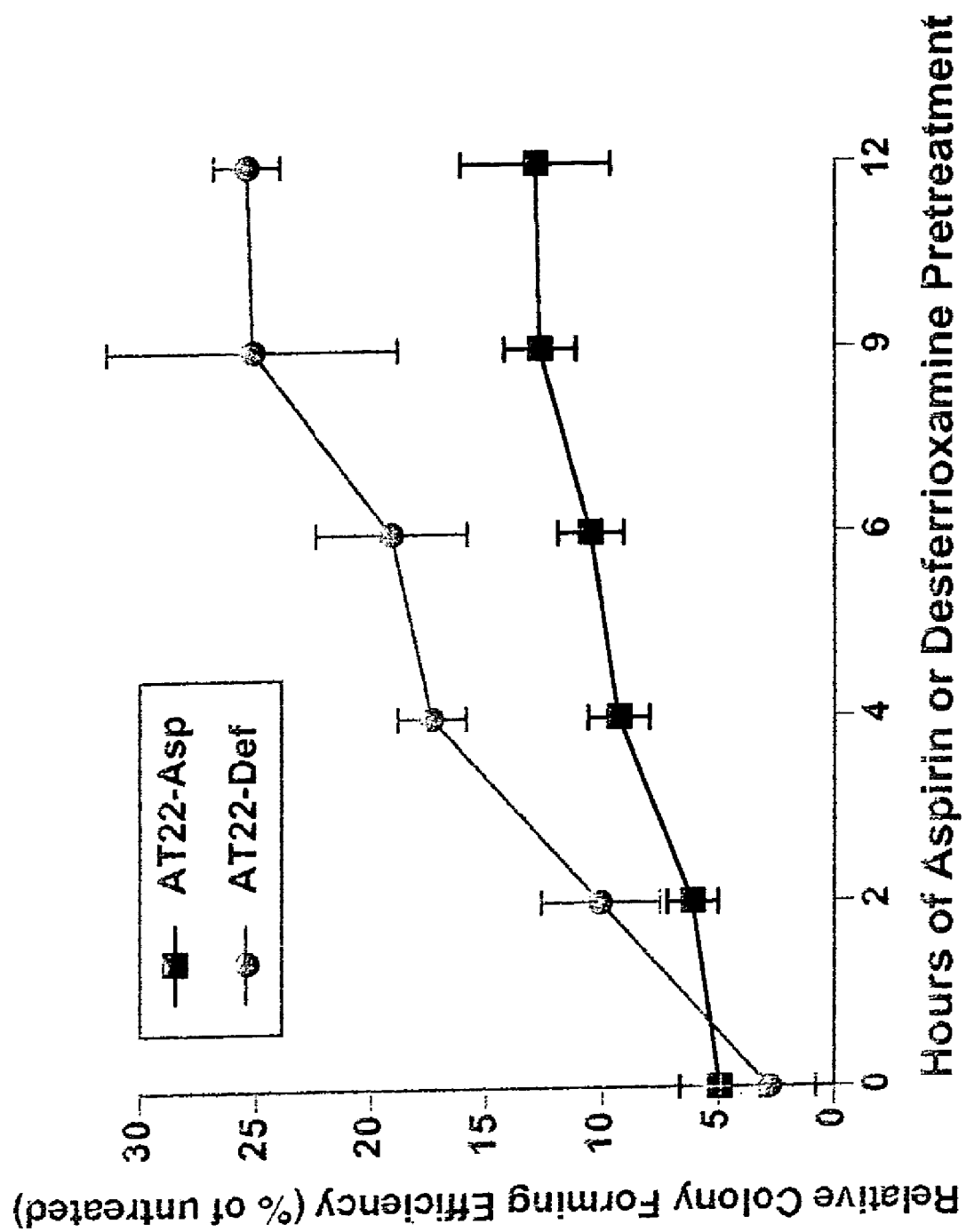
FIG. 9: is a standard curve showing cell survival data of AT22 cells pretreated with desferrioxamine or aspirin. The results are expressed as a percentage of the survival of untreated cells as measured using a colony forming-efficiency assay. AT22 cellular resistance to the toxic effects of t-BOOH exposure increases with longer exposure to desferrioxamine or aspirin in the colony forming-efficiency assay. [Desferrioxamine], 100 µM; [aspirin], 0.3 mM. Abbreviations in figure legend; Asp, aspirin; Def, desferrioxamine.

Mitotic delay assays were performed as previously described (See R. E. Shackelford et al. The Ataxia telangiectasia Gene Product Is Required for Oxidative Stress-induced G1 and G2 Checkpoint Function in Human Fibroblasts, 276 J. BIOL. CHEM. 21951–21959 (2001)). In brief, cells were plated onto 100 mm tissue culture plates and incubated 48–72 h (to approximately 50% confluency). The cells were then treated with $FeCl_2$ for 15 m as in the colony forming-efficiency assay, washed 2× with media, cultured 2 h, and the media was removed. The cells were fixed in 5 ml cold methanol for 10 min and air-dried. The cells were stained with 0.2 µg/ml 4',6-diamidino-2-phenylindole (DAPI) in water and examined by fluorescence microscopy. The percentage of mitotic cells (mitotic delay) was determined by counts of 5,000 cells. Mitotic delay experiments were performed in triplicate and the standard deviations were calculated as in the colony forming-efficiency assays. (FIG. 3).

Example 3

Western Blot Analysis

Figure 15:
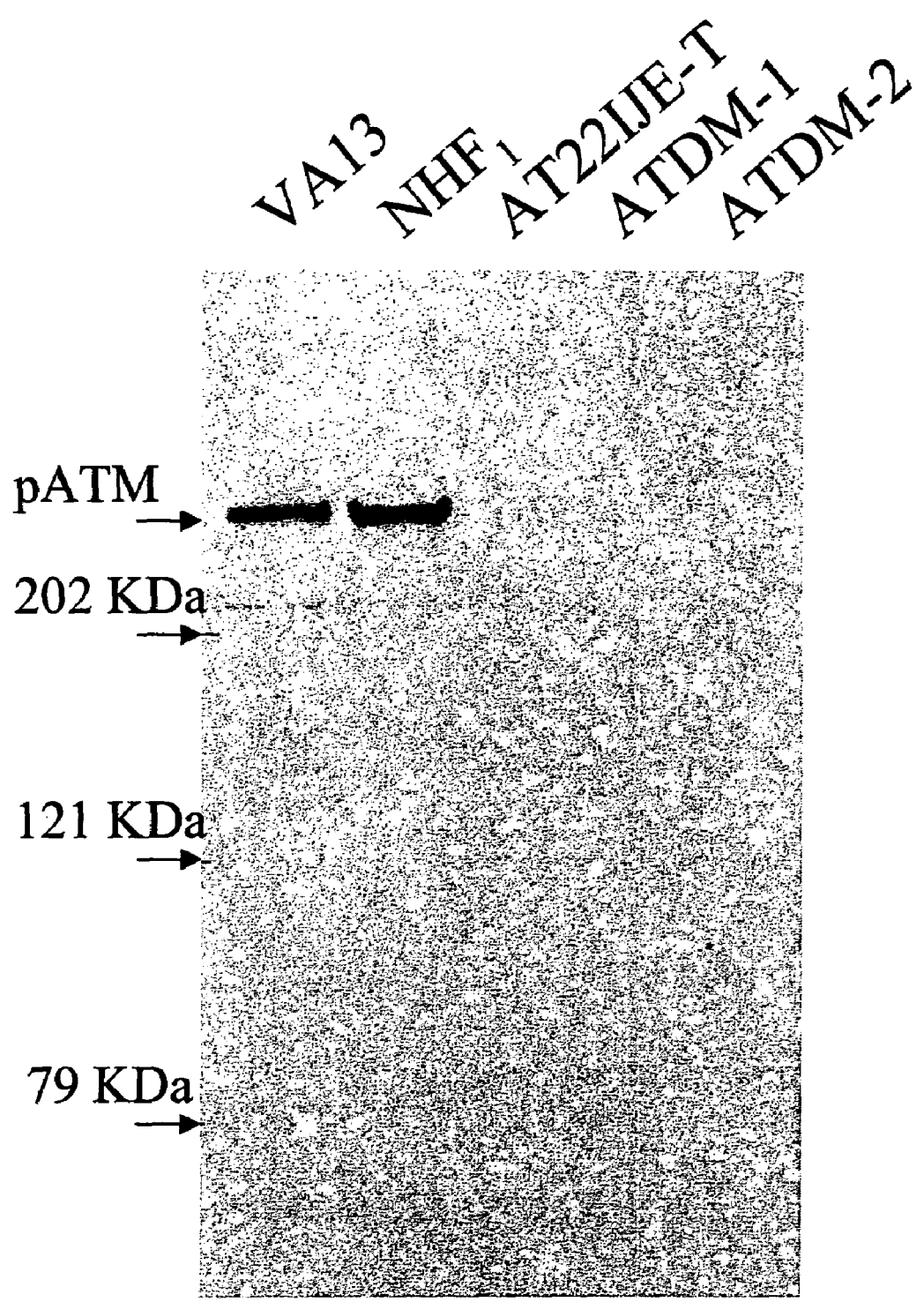
FIG. 15: the results of western blot analysis with VA13, NHF1, AT22, ATDM-1, ATDM-2 cells.

Cells on 100 mm tissue culture plates were washed 3× with phosphate buffered saline, harvested by scraping, and pelleted at 1000 g for 5 min. The resulting cell pellets were resuspended in 250 µl 1× lysis buffer (1% NP-40, 10 mM Sodium Phosphate [dibasic], 1 mM EDTA, 5 mM glycerol phosphate, 1 mM DTT, 150 mM NaCl), with protease inhibitors (Aprotonin 4.0 g/ml, Leupeptin 0.75 µ/ml, Phenylmathanesulfonyl Fluoride 340 µg/ml) and placed into a microcentrifuge tube. The suspension was centrifuged at 4C for 20 min at 13000 g and the supernatant, total cellular protein, was put into a microfuge tube for protein quantification. Primary antibody N514 (kindly provided by Dr. R. Paules at the National Institute of Environmental Health Sciences) was added to each protein sample and tumbled 2 h at 4C. 20 µl protein G-Sepharose beads were added (GIBCO BRL) and the tubes were tumbled for 30 min. The G-Sepharose beads were washed 3× with in 1 ml lysis buffer with quick spins at 10450 g for −5 sec. 5× loading buffer (10% SDS, 375 mM Tris pH 5.8, 50% glycerol, 0.01% bromophenol blue) was then added to each sample and boiled 5 min. The samples were centrifuged at 13650 g for 5 min, the supernatants collected, and loaded onto a Novex 3–8% gradient gel per manufactures suggested protocol. The gel was run 90 min at 150 V. The gel was transferred onto nitrocellulose 7 h at 90 V at which time it was turned down to 35 V overnight. The blot was rinsed with 1×TBST (20 mM Tris pH 8.0, 150 mM NaCl, 0.05% Tween-20) and the nitrocellulose was blocked with 5% powered milk in 1×TBST for 3 h. The blot was rinsed with 1×TBST and then Gene Tex ATM-2C1 was added at 1:1,000 dilution for 1 h. The blot was washed 3× for 10 min with 1×TBST. Amersham NA931 was added for 1 h, 1:4000. The blot was washed 3× 10 min with TBST and developed using the Roche ECL kit. (FIG. 15).

Example 4

Materials

FeCl2, apoferritin, (NH4)2Fe(SO4)2, CuCl2, bathophenantroline disulphonate (BPS), hygromycin, and desferrioxamine mesylate were obtained from Sigma Chemical Corp (St. Louis, Mo.). Fetal calf serum (FCS) and Dulbecco's Modified Eagle's Medium (DMEM) were obtained from Invitrogen (Rockville, Md.). Culture dishes were obtained from Becton Dickinson (Franklin Lakes, N.J.).

The Human Ferritin Quantification ELISA Kit (Cat. #1810) was purchased from Alpha Diagnostic International, San Antonio, Tex. and used according the manufacturer's protocol.

Colony Forming-Efficiency Assay

Preparation of cells is as described previously in Example 1. Colony forming-efficiency experiments were performed as previously described (See R. E. Shackelford et al. The Ataxia telangiectasia Gene Product Is Required for Oxidative Stress-induced G1 and G2 Checkpoint Function in Human Fibroblasts, 276 J. BIOL. CHEM. 21951–21959 (2001)). In brief, exponentially growing cells were plated at 2,000 cells/100 mm tissue culture dish in 10 ml appropriate media with an added iron chelating agent and cultured for 14 days. The resulting colonies were fixed and stained after 14 days culture by water:methanol addition (1:1) containing crystal violet (1 g/L). Colonies consisting of cell clusters containing greater than 50 cells were counted under a dissecting microscope. For experiments involving apoferritin or quercetin pre-exposure on t-BOOH resistance, the cells were allowed to adhere 6 h in increasing aopferritin or quercetin concentrations, washed 4× with 3 ml media, treated with 10 mM t-BOOH, washed 1× with 3 ml media, and allowed to grow for 14 days in 10 ml appropriate media. Data indicates survival as a percentage of untreated cells. The AT22 and VA13 tumor cell lines were used at passages 20–40. The primary NHF1, ATDM-1, and ATDM-2 cell strains were used at passages 6–19. All experiments were done at least twice in triplicate. Standard deviations (error bars) were calculated from each experimental data point divided by the mean untreated value and averaged between triplicate experiments to obtain the mean standard deviation. (FIGS. 11A–14C).

Example 5

Mouse AT Status Typing

AT heterozygous mice were obtained from The Jackson Laboratory (Bar Harbor, Me.) and were cared for under approval an animal protocol using American Association for Laboratory Animal Science guidelines. Heterozygous mice pairs were bred and AT and wild type mice were identified by extracting 35–70 ml of blood from the Saphenous vein of the mice with heparinzed microcapillary tubes. The blood was transferred to a microfuge tube 20 ml of 10 mM EDTA, mixed, and stored on ice. 200 ml lysis buffer (0.32 M Sucrose, 10 mM Tris-HCl pH 7.5, 5 mM MgCl2, 1% v/v Triton X-100) was added to each tube. The tubes were vortexed and centrifuged at 16,000 g to pellet the nuclei. The samples were washed 4× with lysis buffer and centrifuged as before. The nuclei pellets were resuspended in 50–100 ml of digestion buffer (50 mM KCl, 10 mM Tris-HCl pH 8.3, 2.5 mM MgCl2, 0.1 mg/ml gelatin, 0.45% [v/v] Nonidet P40, 0.45% [v/v] Tween 20). The solution was autoclaved to sterilize and dissolve the gelatin. Proteinase K, at a final working concentration of 60 mg/ml, was added immediately prior to use. The resulting solution was incubated at 55C overnight, heated to 97C for 10 min to inactivate the proteinase K, and PCR was performed on 2 ml of the samples using 4 primers designed to amplify either the Neo genetic markers or the ATM gene. The PCR reactions were run into a 1.5% argarose gel. the wild type mice had only one band at 147 bp utilizing the Neo primers. The mutant AT mice had only one band at 280 bp utilizing the AT primers (For PCR reaction conditions, primer sequences, and cycling conditions, see JAX®Mice Protocol Index available at http://jaxmicejax.org/pub-cgi/protocols/
protocols.sh?objtype=protocol&protocol_id=220).

Example 6

AT and Normal Murine Seras

The AT and normal murine seras were obtained via cardiac the puncture of freshly sacrificed mice. The blood from each mouse was allowed to clot in a 1.5 ml eppendorf tube for 30 min at room temp. After 30 min the blood was centrifuged at 9,000 g for 5 min and the upper sera layer was removed. The sera was immediately used to quantify labile ferrous iron. All mice were littermates between 20 and 35 days old and all mice were the same age when labile iron concentrations were quantified. The sera from each mouse was measured separately. The seras of 4 normal and 7 AT mice were quantified in two separate experiments.

Quantification of Labile Ferrous Iron

The concentration of labile ferrous iron in normal and AT mouse sera was quantified as previously described (See U. A. Nilsson et al. A Simple and Rapid Method for the Determination of "Free" Iron in Biological Fluids, 36 FREE RADIC RES. 677–684 (2002)). In brief, a 50 mM stock solution of BPS was prepared by dissolving 28.2 mg BPS on 1 ml of deionized pyrogen free water. A standard curve for ferrous iron was constructed by dissolving 196 mg (NH4)2Fe(SO4)2 in 500 ml deionized pyrogen free water. The solution was then diluted to make 0.1 to 30 mM (NH4)2Fe(SO4)2 solutions. 10 ml of each of these solutions were added to 490 ml of water or each (NH4)2Fe(SO4)2 solution, mixed, and left for 15 min to insure complete complex formation. 50 ml of each sample was then transferred to a 96 well plate and the absorbance was read at 535 nm against a water blank. For serum labile ferrous iron measurements 49 ml of each sera sample received either 1 ml of BPS stock solution of 1 ml water and was gently mixed a 96 plate well. After 15 min, the absorbance was read at 535 nm with the standard curve. The value of each respective blank was subtracted from each of the samples containing the BPS complex. Data was analyzed using a student's t-test demonstrating a significant difference between the means of wild-type and AT mouse sera (P=0.013). (FIG. 1).

REFERENCES

1. M. F. Lavin, Y. Shiloh, The Genetic Defect in Ataxia-telangiectasia, 15 ANNU. REV. IMMUNOL. 177–202 (1997).

2. M. M. Weil et al. Radiation Induces Genomic Instability and Mammary Ductal Dysplasia in ATM Heterozygous Mice, 20(32) ONCOGENE 4409–11 (2001).

3. Y. Shiloh et al. In Vitro Phenotype of Ataxia-telangiectasia (AT) Fibroblast Strains: Clues to the Nature of the "AT DNA Lesion" and the Molecular Defect in AT, 19 KROC FOUND SER. 111–21 (1985).

4. Y. Shiloh et al. Cells from Patients with Ataxia telangiectasia Are Abnormally Sensitive to the Cytotoxic Effect of a Tumor Promoter, Phorbol-12-Myristate-13-Acetate, 149 (2) MUTAT RES. 283–86 (1985).

5. Barzilai et al. ATM Deficiency and Oxidative Stress: a New Dimension of Defective Response to DNA Damage, 1 DNA REPAIR 3–25 (2002).

6. D. Watters et al. Localization of a Portion of Extra-nuclear ATM to Peroxisomes, 274 J. BIOL. CHEM. 34277–34282 (1999).

7. M. J. Meredith & M. L. Dodson, Impaired Glutathione Biosynthesis in Cultured Human Ataxia-telangiectasia Cells, 47 CANCER RES. 4576–4581 (1987).

8. M. Gatei et al. Ataxia-telangiectasia: Chronic Activation of Damage-Responsive Functions Is Reduced By Alpha-lipoic Acid, 20 ONCOGENE 289–294 (2001).

9. J. Reichenback et al. Elevated Oxidative Stress in Patients with Ataxia Telangiectasia, 4 ANTIOXIDANTS REDOX. SIG. 465–469 (2002).

10. Kamsler et al. Increased Oxidative Stress in Ataxia-telangiectasia Evidenced by Alterations in Redox State of Brains from Atm-deficient Mice, 61 CANCER RES. 1849–1854 (2001).

11. Y. Ziv et al. 15 Recombinant ATM Protein Complements the Cellular A-T Phenotype, ONCOGENE 159–167 (1997).

12. R. E. Shackelford et al. The Ataxia telangiectasia Gene Product Is Required for Oxidative Stress-induced G1 and G2 Checkpoint Function in Human Fibroblasts, 276 J. BIOL. CHEM. 21951–21959 (2001).

13. L. Ha et al. Chromium (VI) Activates Ataxia Telangiectasia Mutated (ATM) Protein. Requirement of ATM for Both Apoptosis and Recovery from Terminal Growth Arrest, 278 J. BIOL. CHEM. 17885–17894 (2003).

14. L. J. Hofseth et al. Nitric Oxide-induced Cellular Stress and p53 Activation in Chronic Inflammation, 100 PROC. NATL. ACAD. SCI. USA 143–148 (2003).

15. M. H. L. Green et al. Hypersensitivity of Ataxia-telangiectasia Fibroblasts to a Nitric Oxide Donor, 22 FREE RADICAL BIOL. MED. 343–347 (1997).

16. M. Vuillaume et al. Stimulated Production of ATP by H2O2 Disproportionation in Extracts from Normal and Xeroderma Pigmentosum Skins, and from Normal, Xeroderma Pigmentosum, Ataxia telangiectasia and Simian Virus 40 Transformed Cell Lines, 10 CARCINOGENESIS 1375–1381 (1989).

17. J. Ward et al. Response of Fibroblast Cultures from Ataxia-telangiectasia Patients to Reactive Oxygen Species Generated During Inflammatory Reactions, 24 ENVIRON. MOL. MUTAGEN. 103–111 (1994).

18. D. Menendez et al. ATM Status Confers Sensitivity to Arsenic Cytotoxic Effects, 16 MUTAGENESIS 443–448 (2001).

19. M. Martin et al. Radiation-induced Chromosome Breaks in Ataxia-telangiectasia Cells Remain Open, 79(3) INT. J. RADIATBIOL. 203–10 (2003).

20. Tchirkov & P. M. Lansdorp. Role of Oxidative Stress in Telomere Shortening in Cultured Fibroblasts from Normal Individuals and Patients with Ataxia-telangiectasia, 12(3) HUM. MOL. GENET. 227–32 (2003).

21. R. E. Shackelford et al. The Ataxia telangiectasia Gene Product Is Required for Oxidative Stress-induced G1 and G2 Checkpoint Function in Human Fibroblasts, 276(24) J. BIOL. CHEM. 21951–59 (2001).

22. M. F. Lavin & Y. Shiloh, The Genetic Defect in Ataxia-telangiectasia, 15 ANNU. REV. IMMUNOL. 177–202 (1997).

23. K. K. Wong et al. Telomere Dysfunction and Atm Deficiency Compromises Organ Homeostasis and Accelerates Ageing, 421(6923) NATURE 643–48 (2003).

24. U. A. Nilsson et al. A Simple and Rapid Method for the Determination of "Free" Iron in Biological Fluids, 36 FREE RADIC RES. 677–684 (2002).

25. K. L. Quick, & L. L. Dugan, Superoxide Stress Identifies Neurons at Risk in a Model of Ataxia-telangiectasia, 49 ANN NEUROL. 627–635 (2001).

26. D. Watters et al. Localization of a Portion of Extra-nuclear ATM to Peroxisomes, J. BIOL. CHEM. 274, 34277–34282 (1999).

We claim:

1. A method for treating AT by administering to an animal a therapeutically effective amount of a chelating agent and a pharmaceutically acceptable carrier.

2. The method of claim 1 wherein treatment additionally comprising administering a therapeutically effective amount of an antioxidant.

3. The method of claim 1 wherein the chelating agent additionally comprises substances capable of binding any transition metal.

4. The method of claim 1 wherein the chelating agent is selected from the group consisting of ferrioxamine, trihydroxaniic acid, CP94, EDTA, desferrioxamine hydroxaniic acids, deferoxamine B (DFO) as the methanesulfonate salt, also known as desferrioxanilne B mesylate (DFOM), desferal from Novartis (previously Ciba-Giegy), apoferritin, CDTA (trans-1,2-diaminocyclohexane-N,N,N',N'-tetraacetic acid), and DTPA (diethylenetriamine-N,N,N',N'',N''-penta-acetic acid), and a pharmaceutically acceptable chelating agent of iron thereof.

5. The method of claim 1 wherein the chelating agent is capable of crossing cell membranes.

6. The method of claim 1 wherein the chelating agent is selected from the group consisting of penecillamine, triene, bathocuproine disulfonate, diethylenetri amine pentaacetic acid, and a pharmaceutically acceptable chelating agent of copper thereof.

7. The method of claim 2 wherein the antioxidant is a flavonoid or a derivative thereof.

8. The method of claim 7 wherein the flavonoid is selected from the group of quercetin, morn, naringenin and hesperetin, taxifolin, afzelin, quercitrin, myricitrin, genistein, apigenin and biochanin A, flavone, flavopiridol; the soy isoflavonoid, genistein; the tea catechin epigallocatechin gallate; flavonol, epicatechin, hesperetin, chrysin, diosmin, hesperidin, luteolin, and rutin.

9. The method of claim 1 wherein the cell or animal is under oxidative stress.

10. The method of claim 1 wherein a substance that additionally induces a chelating agent to bind a transition metal is administered.

11. A method for treating AT by administering to cells a therapeutically effective amount of a chelating agent and a pharmaceutically acceptable carrier so that genomic stability in said cells is increased compared to cells that were not treated as quantified in viability assays.

12. The method of claim 11 wherein treatment additionally comprises administering a therapeutically effective amount of an antioxidant.

13. The method of claim 11 wherein the chelating agent additionally comprises substances capable of binding any transition metal.

14. The method of claim 11 wherein the chelating agent is selected from the group consisting of ferrioxarnine, trihydroxamic acid, CP94, EDTA, desferrioxamine hydroxainic acids, deferoxamine B (DFO) as the methanesulfonate salt, also known as desferrioxamine B mesylate (DFOM), desferal from Novartis (previously Ciba-Giegy), apoferritin, CDTA (trans-19,2-diaminocyclohexane-N,N,N',N'-tetraacetic acid), and DTPA (diethylenetriamine-N,N,N',N'',N''-penta-acetic acid), and a pharmaceutically acceptable chelating agent of iron thereof.

15. The method of claim 11 wherein the chelating agent is capable of crossing cell membranes.

16. The method of claim 11 wherein the chelating agent is selected from the group consisting of penecillamine, triene, bathocuproine disulfonate, diethylenetriamine pentaacetic acid, and a pharmaceutically acceptable chelating agent of copper thereof.

17. The method of claim 12 wherein the antioxidant is a flavonoid or a derivative thereof.

18. The method of claim 17 wherein the flavonoid is selected from the group of quercetin, morn, naringenin and hesperetin, taxifolin, afzelin, quercitrin, myricitrin, genistein, apigenin and biochanin A, flavone, flavopindol; the soy isoflavonoid, genistein; the tea catechin epigallocatechin gallate; flavonol, epicatechin, hesperetin, chrysin, diosmin, hesperidin, luteolin, and rutin.

19. The method of claim 11 wherein the cell or animal is under oxidative stress.

20. The method of claim 11 wherein a substance that additionally induces a chelating agent to bind a transition metal is administered.

21. A method for treating AT by administering to cells a therapeutically effective amount of a chelating agent and a pharmaceutically acceptable carrier so that oxidative stress in said cells in decreased compared to cells that were not treated as quantified in viability assays.

22. The method of claim 21 wherein treatment additionally comprises administering a therapeutically effective amount of an antioxidant.

23. The method of claim 21 wherein the chelating agent additionally comprises substances capable of binding any transition metal.

24. The method of claim 21 wherein the chelating agent is selected from the group consisting of ferrioxamine, trihydroxamic acid, CP94, EDTA, desferrioxamine hydroxamic acids, deferoxamine B (DFO) as the methanesulfonate salt, also known as desferrioxamine B mesylate (DFOM), desferal from Novartis (previously Ciba-Giegy), apoferritin, CDTA (trans-33,2-diaminocyclohexane-N,N,N',N'-tetraacetic acid), and DTPA (diethylenetriamine-N,N,N',N'',N''-penta-acetic acid), and a pharmaceutically acceptable chelating agent of iron thereof.

25. The method of claim 21 wherein the chelating agent is capable of crossing cell membranes.

26. The method of claim 21 wherein the chelating agent is selected from the group consisting of penecillamine, triene, bathocuproine disulfonate, diethylenetriamine pentaacetic acid, and a pharmaceutically acceptable chelating agent of copper thereof.

27. The method of claim 22 wherein the antioxidant is a flavonoid or a derivative thereof.

28. The method of claim 27 wherein the flavonoid is selected from the group of quercetin, morn, naringenin and hesperetin, taxifolin, afzelin, quercitrin, myricitrin, genistein, apigenin and biochanin A, flavone, flavopiridol; the soy isoflavonoid, genistein; the tea catechin epigallocatechin gallate; flavonol, epicatechin, hesperetin, chrysin, diosmin, hesperidin, luteolin, and rutin.

29. The method of claim 21 wherein the cell or animal is under oxidative stress.

30. The method of claim 21 wherein a substance that additionally induces a chelating agent to bind a transition metal is administered.

31. A method for treating AT by administering to an animal a therapeutically effective amount of a chelating agent and a pharmaceutically acceptable carrier and an antioxidant.

32. A method for treating AT by administering a therapeutically effective amount of an antioxidant.

33. The method of claim 32 wherein the antioxidant is a flavonoid or a derivative thereof.

34. The method of claim 33 wherein the flavonoid is selected from the group of quercetin, morn, naringenin and hesperetin, taxifolin, afzelin, quercitrin, myricitrin, genistein, apigenin and biochanin A, flavone, flavopiridol; the soy isoflavonoid, genistein; the tea catechin epigallocatechin gallate; flavonol, epicatechin, hesperetin, chrysin, diosmin, hesperidin, luteolin, and rutin.

35. The method of claim 32 wherein the cell or animal is under oxidative stress.

36. A pharmaceutical composition for treating AT comprising a chelating agent and a pharmaceutically acceptable carrier.

37. The pharmaceutical composition of claim 36 wherein the composition additionally comprises a therapeutically effective amount of an antioxidant.

38. The pharmaceutical composition of claim 36 wherein the chelating agent additionally comprises substances capable of binding any transition metal.

39. The pharmaceutical composition of claim 36 wherein the chelating agent is selected from the group consisting of ferrioxamine, trihydroxamic acid, CP94, EDTA, desferrioxamine hydroxamic acids, deferoxainine B (DFO) as the methanesulfonate salt, also known as desferrioxanilne B mesylate (DFOM), desferal from Novartis (previously Ciba-Giegy), apoferritin, CDTA (trans-1,2-diaminocyclohexane-N,N,N',N'-tetraacetic acid), and DTPA (diethylenetriamine-N,N,N',N'',N''-penta-acetic acid), and a pharmaceutically acceptable chelating agent of iron thereof.

40. The pharmaceutical composition of claim 36 wherein the chelating agent is capable of crossing cell membranes.

41. The pharmaceutical composition of claim 36 wherein the chelating agent is selected from the group consisting of penecillamine, triene, bathocuproine disulfonate, diethylenetriamine pentaacetic acid, and a pharmaceutically acceptable chelating agent of copper thereof.

42. The pharmaceutical composition of claim 37 wherein the antioxidant is a flavonoid or a derivative thereof.

43. The pharmaceutical composition of claim 42 wherein the flavonoid is selected from the group of quercetin, morin, naringenin and hesperetin, taxifolin, afzelin, quercitrin, myricitrin, genistein, apigenin and biochanin A, flavone, flavopiridol; the soy isoflavonoid, genistein; the tea catechin epigallocatechin gallate; flavonol, epicatechin, hesperetin, chrysin, diosmin, hesperidin, luteolin, and rutin.

* * * * *